US012691262B2

(12) United States Patent
Wang

(10) Patent No.: US 12,691,262 B2
(45) Date of Patent: Jul. 28, 2026

(54) METHOD FOR TREATMENT OF AIRWAY STRICTURE OR STENOSIS

(71) Applicant: Airiver Medical, Inc., Dover, NV (US)

(72) Inventor: Lixiao Wang, Dover, NV (US)

(73) Assignee: Airiver Medical, Inc., Dover, NV (US)

( * ) Notice: Subject to any disclaimer, the term of this patent is extended or adjusted under 35 U.S.C. 154(b) by 49 days.

(21) Appl. No.: 18/709,120

(22) PCT Filed: Nov. 16, 2022

(86) PCT No.: PCT/US2022/050087
§ 371 (c)(1),
(2) Date: May 10, 2024

(87) PCT Pub. No.: WO2023/091475
PCT Pub. Date: May 25, 2023

(65) Prior Publication Data
US 2025/0025673 A1 Jan. 23, 2025

Related U.S. Application Data

(60) Provisional application No. 63/279,776, filed on Nov. 16, 2021.

(51) Int. Cl.
*A61M 25/10* (2013.01)
*A61L 29/08* (2006.01)
*A61L 29/16* (2006.01)

(52) U.S. Cl.
CPC ....... *A61M 25/10184* (2013.11); *A61L 29/08* (2013.01); *A61L 29/16* (2013.01);
(Continued)

(58) Field of Classification Search
CPC ....... A61M 25/10184; A61M 2025/105; A61L 29/08; A61L 29/16; A61L 2300/416; A61L 2420/00
See application file for complete search history.

(56) References Cited

U.S. PATENT DOCUMENTS

| 4,254,056 A | 3/1981 | Konno et al. |
| 4,573,966 A | 3/1986 | Weikl et al. |

(Continued)

FOREIGN PATENT DOCUMENTS

| CN | 1593359 A | 3/2005 |
| CN | 101035593 A | 9/2007 |

(Continued)

OTHER PUBLICATIONS

"Japanese Application Serial No. 2022-178135, Final Notification of Reasons for Rejection mailed Jan. 7, 2025", W English Translation, 8 pgs.

(Continued)

*Primary Examiner* — Dung T Ulsh
(74) *Attorney, Agent, or Firm* — Schwegman, Lundberg & Woessner, P.A.

(57) ABSTRACT

A method of treating a recurring airway stricture or stenosis in a body lumen includes inserting a scope and a drug-coated balloon catheter into a target site comprising the recurring airway stricture or stenosis in the body lumen. The method includes inflating the balloon to an inflation diameter such that the coating contacts an interior of the body lumen at the target site. The method includes deflating the balloon and withdrawing the scope and the balloon catheter from the target site.

19 Claims, 7 Drawing Sheets

(52) U.S. Cl.
CPC ..... *A61L 2300/416* (2013.01); *A61L 2420/00* (2013.01); *A61M 2025/105* (2013.01); *A61M 2202/0085* (2013.01)

(56) References Cited

U.S. PATENT DOCUMENTS

| | | | |
|---|---|---|---|
| 4,653,438 A | 3/1987 | Russell |
| 4,684,363 A | 8/1987 | Ari et al. |
| 5,045,061 A | 9/1991 | Seifert et al. |
| 5,263,931 A | 11/1993 | Miller |
| 5,314,443 A | 5/1994 | Rudnick |
| 5,315,992 A | 5/1994 | Dalton |
| 5,380,284 A | 1/1995 | Don |
| 5,419,763 A | 5/1995 | Hildebrand |
| 5,423,755 A | 6/1995 | Kesten et al. |
| 5,460,610 A | 10/1995 | Don |
| 5,599,307 A | 2/1997 | Bacher et al. |
| 5,681,281 A | 10/1997 | Vigil et al. |
| 5,720,735 A | 2/1998 | Dorros |
| 6,048,332 A | 4/2000 | Duffy et al. |
| 6,062,223 A | 5/2000 | Palazzo et al. |
| 6,135,981 A | 10/2000 | Dyke |
| 6,148,222 A | 11/2000 | Ramsey, III |
| 6,217,554 B1 | 4/2001 | Green |
| 6,258,087 B1 | 7/2001 | Edwards et al. |
| 6,444,233 B1 | 9/2002 | Arntzen et al. |
| 6,623,452 B2 | 9/2003 | Chien et al. |
| 6,685,672 B1 | 2/2004 | Forman |
| 7,617,005 B2 | 11/2009 | Demarais et al. |
| 7,653,438 B2 | 1/2010 | Deem et al. |
| 7,717,948 B2 | 5/2010 | Demarais et al. |
| 8,052,668 B2 | 11/2011 | Sih |
| 8,128,592 B2 | 3/2012 | Mitelberg et al. |
| 8,372,054 B2 | 2/2013 | Duffy et al. |
| 8,620,423 B2 | 12/2013 | Demarais et al. |
| 8,740,849 B1 | 6/2014 | Fischell et al. |
| 8,774,913 B2 | 7/2014 | Demarais et al. |
| 8,840,601 B2 | 9/2014 | Salahieh et al. |
| 9,114,123 B2 | 8/2015 | Vafai et al. |
| 10,286,191 B2 | 5/2019 | Wang et al. |
| 10,537,375 B2 | 1/2020 | Wang |
| 10,758,713 B2 | 9/2020 | Wang et al. |
| 11,382,689 B2 | 7/2022 | Wang |
| 11,517,725 B2 | 12/2022 | Wang et al. |
| 11,648,378 B2 | 5/2023 | Wang et al. |
| 11,684,417 B2 | 6/2023 | Wang |
| 12,005,207 B2 | 6/2024 | Wang et al. |
| 12,193,731 B2 | 1/2025 | Wang |
| 12,208,224 B2 | 1/2025 | Wang et al. |
| 2002/0014238 A1 | 2/2002 | Kotmel |
| 2002/0068953 A1 | 6/2002 | Kokish |
| 2002/0177846 A1 | 11/2002 | Mulier |
| 2003/0066532 A1 | 4/2003 | Gobel |
| 2004/0064150 A1 | 4/2004 | Becker |
| 2004/0089313 A1 | 5/2004 | Utley et al. |
| 2004/0116852 A1 | 6/2004 | Scopton |
| 2004/0267336 A1 | 12/2004 | Morrison et al. |
| 2005/0288639 A1 | 12/2005 | Hibner |
| 2006/0161233 A1 | 7/2006 | Barry et al. |
| 2006/0235474 A1 | 10/2006 | Demarais |
| 2006/0265014 A1 | 11/2006 | Demarais et al. |
| 2006/0282120 A1 | 12/2006 | Sih |
| 2007/0077230 A1 | 4/2007 | Mon |
| 2008/0051721 A1 | 2/2008 | Carter et al. |
| 2008/0114297 A1 | 5/2008 | Barry et al. |
| 2008/0118544 A1 | 5/2008 | Wang |
| 2008/0208118 A1 | 8/2008 | Goldman |
| 2008/0255508 A1 | 10/2008 | Wang |
| 2008/0255509 A1 | 10/2008 | Wang |
| 2008/0275445 A1 | 11/2008 | Every et al. |
| 2009/0192505 A1 | 7/2009 | Askew et al. |
| 2009/0301483 A1 | 12/2009 | Barry et al. |
| 2010/0010470 A1 | 1/2010 | Bates |
| 2010/0087781 A1 | 4/2010 | Adams et al. |
| 2010/0145304 A1 | 6/2010 | Cressman |

| | | | |
|---|---|---|---|
| 2010/0209472 A1 | 8/2010 | Wang |
| 2011/0093000 A1 | 4/2011 | Ogle et al. |
| 2011/0104061 A1 | 5/2011 | Seward |
| 2011/0152683 A1 | 6/2011 | Gerrans et al. |
| 2011/0182912 A1 | 7/2011 | Evans et al. |
| 2011/0218564 A1 | 9/2011 | Drasler et al. |
| 2012/0083809 A1 | 4/2012 | Drasler et al. |
| 2012/0116438 A1 | 5/2012 | Salahieh et al. |
| 2012/0197245 A1 | 8/2012 | Burnett et al. |
| 2012/0209251 A1 | 8/2012 | Bates |
| 2012/0215212 A1 | 8/2012 | Selzer et al. |
| 2012/0259269 A1 | 10/2012 | Meyer |
| 2012/0271277 A1 | 10/2012 | Fischell et al. |
| 2012/0271301 A1 | 10/2012 | Fischell et al. |
| 2013/0053792 A1 | 2/2013 | Fischell et al. |
| 2013/0138082 A1 | 5/2013 | Salahieh et al. |
| 2013/0178910 A1 | 7/2013 | Azamian et al. |
| 2013/0189190 A1 | 7/2013 | Wang |
| 2013/0204068 A1 | 8/2013 | Gnanashanmugam et al. |
| 2013/0245665 A1 | 9/2013 | Scandurra et al. |
| 2014/0243872 A1 | 8/2014 | Cordray |
| 2014/0371736 A1 | 12/2014 | Levin et al. |
| 2015/0005805 A1 | 1/2015 | Kesten et al. |
| 2015/0056298 A1 | 2/2015 | Azamian et al. |
| 2015/0224289 A1 | 8/2015 | Seward |
| 2015/0272666 A1 | 10/2015 | Wang |
| 2015/0305943 A1 | 10/2015 | Hossainy et al. |
| 2016/0135879 A1 | 5/2016 | Beasley et al. |
| 2016/0310200 A1 | 10/2016 | Wang |
| 2017/0007310 A1 | 1/2017 | Rajagopalan et al. |
| 2018/0015264 A1 | 1/2018 | Wang et al. |
| 2018/0185618 A1 | 7/2018 | Sweeney |
| 2019/0015639 A1* | 1/2019 | Wang ................... A61L 29/16 |
| 2019/0038881 A1 | 2/2019 | Wang et al. |
| 2019/0076186 A1 | 3/2019 | Fischell et al. |
| 2019/0167918 A1 | 6/2019 | Fischell et al. |
| 2019/0307507 A1 | 10/2019 | Wang |
| 2019/0388147 A1 | 12/2019 | Wang |
| 2020/0009355 A1 | 1/2020 | Wang et al. |
| 2020/0016379 A1 | 1/2020 | Wang et al. |
| 2020/0086093 A1 | 3/2020 | Wang |
| 2020/0230373 A1 | 7/2020 | Stankus et al. |
| 2020/0360671 A1 | 11/2020 | Wang et al. |
| 2020/0398032 A1 | 12/2020 | Wang et al. |
| 2021/0275784 A1 | 9/2021 | Wang |
| 2021/0275785 A1 | 9/2021 | Wang |
| 2021/0275786 A1 | 9/2021 | Wang |
| 2021/0275787 A1 | 9/2021 | Wang |
| 2022/0233238 A1 | 7/2022 | Wang et al. |
| 2022/0233827 A1 | 7/2022 | Wang et al. |
| 2023/0075851 A1 | 3/2023 | Mayse et al. |
| 2023/0270489 A1 | 8/2023 | Wang |
| 2024/0277976 A1 | 8/2024 | Wang et al. |
| 2024/0277977 A1 | 8/2024 | Wang et al. |
| 2025/0082400 A1 | 3/2025 | Wang |
| 2025/0352774 A1 | 11/2025 | Wang et al. |

FOREIGN PATENT DOCUMENTS

| | | | |
|---|---|---|---|
| CN | 101861184 A | 10/2010 |
| CN | 102481428 A | 5/2012 |
| CN | 102573466 A | 7/2012 |
| CN | 102600546 A | 7/2012 |
| CN | 102639077 A | 8/2012 |
| CN | 102698354 A | 10/2012 |
| CN | 102727986 A | 10/2012 |
| CN | 102743163 A | 10/2012 |
| CN | 107106820 A | 8/2017 |
| CN | 110772311 A | 2/2020 |
| CN | 113040895 A | 6/2021 |
| CN | 114025826 A | 2/2022 |
| CN | 118555975 | 8/2024 |
| CN | 114025826 B | 8/2025 |
| CN | 121177644 | 12/2025 |
| EP | 2497524 A1 | 9/2012 |
| EP | 2914326 B1 | 8/2023 |
| EP | 4230162 | 10/2024 |
| JP | S5769814 A | 4/1982 |
| JP | H04215767 A | 8/1992 |

(56)                 References Cited

FOREIGN PATENT DOCUMENTS

| JP | H07308382 | A | 11/1995 |
| JP | 08508917 | A | 9/1996 |
| JP | 2000279524 | A | 10/2000 |
| JP | 2004035128 | A | 2/2004 |
| JP | 2004180892 | A | 7/2004 |
| JP | 2004528924 | A | 9/2004 |
| JP | 2005506101 | A | 3/2005 |
| JP | 2006502801 | A | 1/2006 |
| JP | 2010078379 | A | 4/2010 |
| JP | 2010519005 | A | 6/2010 |
| JP | 2010528815 | A | 8/2010 |
| JP | 2011519699 | A | 7/2011 |
| JP | 2012505050 | A | 3/2012 |
| JP | 2012508067 | A | 4/2012 |
| JP | 2012517858 | A | 8/2012 |
| JP | 2012524808 | A | 10/2012 |
| JP | 2013517847 | A | 5/2013 |
| JP | 2014524342 | A | 9/2014 |
| JP | 2014527272 | A | 10/2014 |
| JP | 2015536945 | A | 12/2015 |
| JP | 2017533036 | A | 11/2017 |
| JP | 6389185 | B2 | 8/2018 |
| JP | 2018153239 | A | 10/2018 |
| JP | 2020178075 | | 10/2020 |
| JP | 2020189858 | A | 11/2020 |
| JP | 2021046397 | A | 3/2021 |
| JP | 2022017822 | | 1/2022 |
| JP | 2022538239 | A | 9/2022 |
| JP | 2023027052 | A | 3/2023 |
| JP | 2024544038 | | 11/2024 |
| JP | 2024170628 | | 12/2024 |
| JP | 7622980 | | 1/2025 |
| JP | 2025111789 | A | 7/2025 |
| JP | 7725067 | B2 | 8/2025 |
| JP | 2025157576 | A | 10/2025 |
| WO | WO-9421320 | A1 | 9/1994 |
| WO | WO-9618427 | A1 | 6/1996 |
| WO | WO-9717099 | A1 | 5/1997 |
| WO | WO-0119445 | A1 | 3/2001 |
| WO | WO-02051490 | A1 | 7/2002 |
| WO | WO-2006055695 | A1 | 5/2006 |
| WO | WO-2008106357 | A1 | 9/2008 |
| WO | WO-2009076732 | A1 | 6/2009 |
| WO | WO-2009082433 | A2 | 7/2009 |
| WO | WO-2010033686 | A1 | 3/2010 |
| WO | WO-2010124120 | A1 | 10/2010 |
| WO | WO-2011094367 | A1 | 8/2011 |
| WO | WO-2011119159 | A1 | 9/2011 |
| WO | WO-2013026565 | A1 | 2/2013 |
| WO | WO-2013028781 | A1 | 2/2013 |
| WO | WO-2013067382 | A1 | 5/2013 |
| WO | WO-2013090848 | A1 | 6/2013 |
| WO | WO-2014070820 | A2 | 5/2014 |
| WO | WO-2015058296 | A1 | 4/2015 |
| WO | WO-2016070032 | A1 | 5/2016 |
| WO | WO-2020264152 | A1 | 12/2020 |
| WO | WO-2023091475 | A1 | 5/2023 |

OTHER PUBLICATIONS

"Japanese Application Serial No. 2021-576638, Notification of Reasons for Rejection mailed Jan. 7, 2025", W English Translation, 6 pgs.
"Chinese Application Serial No. 202110227749.X, Response filed Dec. 30, 2024 to Office Action mailed Oct. 31, 2024", w english claims, 14 pgs.
"European Application Serial No. 22826521.1, Response to Communication Pursuant to Rules 161 and 162 EPC Filed Dec. 20, 2024", 14 pgs.
"Chinese Application Serial No. 202110227749.X, Decision of Rejection mailed Feb. 20, 2025", w English Translation, 7 pgs.
"U.S. Appl. No. 18/295,961, Notice of Allowance mailed Oct. 1, 2024", 11 pgs.

"U.S. Appl. No. 17/010,271, Notice of Allowance mailed Oct. 1, 2024", 11 pgs.
"U.S. Appl. No. 17/010,271, Corrected Notice of Allowability mailed Oct. 9, 2024", 7 pgs.
"Chinese Application Serial No. 202110227749.X, Office Action mailed Oct. 31, 2024", w English translation, 11 pgs.
"Chinese Application Serial No. 202080046425.X, Response filed Dec. 2, 2024 to Office Action mailed Aug. 1, 2024", w english claims, 16 pgs.
"U.S. Appl. No. 18/144,368, Corrected Notice of Allowability mailed Dec. 16, 2024", 6 pgs.
"European Application Serial No. 24205384.1, Extended European Search Report mailed Dec. 12, 2024", 13 pgs.
Chen, John, "Results of related clinical study described in Declaration", Declaration under 37 C.F.R. section 1.132 filed in U.S. Appl. No. 16/986,717. This application is a continuation in part (CIP) of U.S. Appl. No. 16/986,717., (Year: 2024), 4 pgs.
"Japanese Application Serial No. 2022-169101, Examiners Decision of Final Refusal mailed May 14, 2024", W English Translation, 4 pgs.
"Japanese Application Serial No. 2020-178075, Notification of Reasons for Rejection mailed May 14, 2024", W English Translation, 25 pgs.
"Recording of clinical analysis research association", w English translation No. 5, [Online] Retrieved from the internet: http: www. jrsca.jp contents records contents PDF 5-PDF?, (Feb. 2005), 7 pgs.
"U.S. Appl. No. 17/010,271, Restriction Requirement mailed May 22, 2024", 7 pgs.
"International Application Serial No. PCT US2022 050087, International Preliminary Report on Patentability mailed May 30, 2024", 6 pgs.
"Japanese Application Serial No. 2022-178135, Notification of Reasons for Refusal mailed Jun. 4, 2024", w English translation, 6 pgs.
"U.S. Appl. No. 17/010,271, Response filed Jun. 12, 2024 to Restriction Requirement mailed May 22, 2024", 9 pgs.
"Japanese Application Serial No. 2021-576638, Notification of Reasons for Refusal mailed Jun. 11, 2024", w English Translation, 8 pgs.
"U.S. Appl. No. 18/295,961, Non Final Office Action mailed Jun. 21, 2024", 17 pgs.
"U.S. Appl. No. 18/144,368, Response filed Jul. 2, 2024 to Non Final Office Action mailed Apr. 12, 2024", 11 pgs.
"Chinese Application Serial No. 202110227749.X, Office Action mailed Jul. 10, 2024", w English Translation, 9 pgs.
"Japanese Application Serial No. 2020-178075, Response filed Aug. 13, 2024 to Notification of Reasons for Rejection mailed May 14, 2024", W English Claims, 9 pgs.
"Chinese Application Serial No. 202080046425.X, Office Action mailed Aug. 1, 2024", W English Translation, 16 pgs.
"U.S. Appl. No. 18/144,368, Notice of Allowance mailed Aug. 22, 2024", 9 pgs.
"Japanese Application Serial No. 2022-178135, Response filed Sep. 3, 2024 to Notification of Reasons for Refusal mailed Jun. 4, 2024", w English Claims, 15 pgs.
"Japanese Application Serial No. 2021-576638, Response filed Sep. 3, 2024 to Notification of Reasons for Refusal mailed Jun. 11, 2024", w English claims, 20 pgs.
"Chinese Application Serial No. 202110227749.X, Response filed Sep. 10, 2024 to Office Action mailed Jul. 10, 2024", w current English claims, 19 pgs.
"U.S. Appl. No. 18/295,961, Response filed Sep. 19, 2024 to Non Final Office Action mailed Jun. 21, 2024", 12 pgs.
Sugimoto, Ayurni, "Nervous Control of Glucose Metabolism in the Liver", W English translation Lifestyle Research vol. 3, No. 1, 138-141, (2001), 10 pgs.
"International Application Serial No. PCT/US2015/058296, International Search Report mailed Jan. 21, 2016", 2 pgs.
"International Application Serial No. PCT/US2015/058296, Written Opinion mailed Jan. 21, 2016", 7 pgs.
"U.S. Appl. No. 14/438,411, Advisory Action mailed Apr. 30, 2019", 3 pgs.

(56)  References Cited

OTHER PUBLICATIONS

"U.S. Appl. No. 14/438,411, Final Office Action mailed Feb. 25, 2019", 15 pgs.

"U.S. Appl. No. 14/438,411, Final Office Action mailed May 9, 2018", 9 pgs.

"U.S. Appl. No. 14/438,411, Non Final Office Action mailed Sep. 21, 2018", 11 pgs.

"U.S. Appl. No. 14/438,411, Non Final Office Action mailed Oct. 20, 2017", 9 pgs.

"U.S. Appl. No. 14/438,411, Preliminary Amendment filed Jul. 28, 2015", 9 pgs.

"U.S. Appl. No. 14/438,411, Response filed Jan. 17, 2018 to Non Final Office Action mailed Oct. 20, 2017", 9 pgs.

"U.S. Appl. No. 14/438,411, Response filed Apr. 16, 2019 to Final Office Action mailed Feb. 25, 2019", 18 pgs.

"U.S. Appl. No. 14/438,411, Response filed Aug. 7, 2018 to Final Office Action mailed May 9, 2018", 12 pgs.

"U.S. Appl. No. 14/438,411, Response filed Aug. 25, 2017 to Restriction Requirement mailed Jul. 14, 2017", 7 pgs.

"U.S. Appl. No. 14/438,411, Response filed Oct. 8, 2018 to Non Final Office Action mailed Sep. 21, 2018", 17 pgs.

"U.S. Appl. No. 14/438,411, Restriction Requirement mailed Jul. 14, 2017", 8 pgs.

"U.S. Appl. No. 15/133,976, Advisory Action mailed Jul. 30, 2019", 7 pgs.

"U.S. Appl. No. 15/133,976, Corrected Notice of Allowability mailed Nov. 20, 2019", 3 pgs.

"U.S. Appl. No. 15/133,976, Final Office Action mailed May 3, 2019", 15 pgs.

"U.S. Appl. No. 15/133,976, Final Office Action mailed Aug. 16, 2018", 26 pgs.

"U.S. Appl. No. 15/133,976, Non Final Office Action mailed Feb. 15, 2018", 16 pgs.

"U.S. Appl. No. 15/133,976, Non Final Office Action mailed Nov. 30, 2018", 14 pgs.

"U.S. Appl. No. 15/133,976, Notice of Allowance mailed Oct. 1, 2019", 12 pgs.

"U.S. Appl. No. 15/133,976, Preliminary Amendment filed Apr. 20, 2016", 7 pgs.

"U.S. Appl. No. 15/133,976, Response filed Mar. 20, 2019 to Non Final Office Action mailed Nov. 30, 2018", 17 pgs.

"U.S. Appl. No. 15/133,976, Response filed Jun. 14, 2018 to Non Final Office Action mailed Feb. 15, 2018", 13 pgs.

"U.S. Appl. No. 15/133,976, Response filed Jul. 1, 2019 to Final Office Action mailed May 3, 2019", 20 pgs.

"U.S. Appl. No. 15/133,976, Response filed Oct. 26, 2018 to Final Office Action mailed Aug. 16, 2018", 20 pgs.

"U.S. Appl. No. 15/133,976, Response filed Dec. 27, 2017 to Restriction Requirement mailed Oct. 31, 2017", 8 pgs.

"U.S. Appl. No. 15/133,976, Restriction Requirement mailed Oct. 31, 2017", 7 pgs.

"U.S. Appl. No. 15/521,973, Examiner Interview Summary mailed Jun. 4, 2018", 3 pgs.

"U.S. Appl. No. 15/521,973, Final Office Action mailed Jan. 15, 2019", 16 pgs.

"U.S. Appl. No. 15/521,973, Non Final Office Action mailed May 18, 2018", 21 pgs.

"U.S. Appl. No. 15/521,973, Non Final Office Action mailed Sep. 14, 2018", 15 pgs.

"U.S. Appl. No. 15/521,973, Notice of Allowance mailed Mar. 27, 2019", 7 pgs.

"U.S. Appl. No. 15/521,973, Preliminary Amendment filed Apr. 26, 2017", 8 pgs.

"U.S. Appl. No. 15/521,973, Response filed Mar. 14, 2019 to Final Office Action mailed Jan. 15, 2019", 16 pgs.

"U.S. Appl. No. 15/521,973, Response filed Dec. 10, 2018 to Non Final Office Action mailed Sep. 14, 2018", 11 pgs.

"U.S. Appl. No. 16/156,163, Non Final Office Action mailed Apr. 2, 2020", 7 pgs.

"U.S. Appl. No. 16/156,163, Notice of Allowance mailed Jul. 22, 2020", 5 pgs.

"U.S. Appl. No. 16/156,163, Response filed Jul. 1, 2020 to Non Final Office Action mailed Apr. 2, 2020", 9 pgs.

"U.S. Appl. No. 16/419,587, Corrected Notice of Allowability mailed Apr. 27, 2022", 5 pgs.

"U.S. Appl. No. 16/419,587, Final Office Action mailed Feb. 24, 2022", 18 pgs.

"U.S. Appl. No. 16/419,587, Non Final Office Action mailed Oct. 5, 2021", 15 pgs.

"U.S. Appl. No. 16/419,587, Notice of Allowance mailed Apr. 11, 2022", 8 pgs.

"U.S. Appl. No. 16/419,587, Preliminary Amendment filed Jul. 9, 2019", 3 pgs.

"U.S. Appl. No. 16/419,587, Response filed Mar. 9, 2022 to Final Office Action mailed Feb. 24, 2022", 12 pgs.

"U.S. Appl. No. 16/419,587, Response filed Nov. 4, 2021 to Non Final Office Action mailed Oct. 5, 2021", 12 pgs.

"U.S. Appl. No. 16/563,192, Non Final Office Action mailed Nov. 30, 2022", 21 pgs.

"U.S. Appl. No. 16/563,192, Notice of Allowance mailed Mar. 8, 2023", 8 pgs.

"U.S. Appl. No. 16/563,192, Response filed Feb. 9, 2023 to Non Final Office Action mailed Nov. 30, 2022", 13 pgs.

"U.S. Appl. No. 16/563,213, Non Final Office Action mailed Sep. 15, 2022", 9 pgs.

"U.S. Appl. No. 16/563,213, Notice of Allowability mailed Mar. 1, 2023", 4 pgs.

"U.S. Appl. No. 16/563,213, Notice of Allowance mailed Feb. 3, 2023", 7 pgs.

'U.S. Appl. No. 16/563,213, Response filed Dec. 13, 2022 to Non Final Office Action mailed Sep. 15, 2022, 7 pgs.

"U.S. Appl. No. 16/563,235, Non Final Office Action mailed May 12, 2022", 16 pgs.

"U.S. Appl. No. 16/563,235, Non Final Office Action mailed Sep. 30, 2021", 13 pgs.

"U.S. Appl. No. 16/563,235, Notice of Allowance mailed Feb. 11, 2022", 7 pgs.

"U.S. Appl. No. 16/563,235, Notice of Allowance mailed Aug. 26, 2022", 7 pgs.

"U.S. Appl. No. 16/563,235, Response filed Aug. 11, 2022 to Non Final Office Action mailed May 12, 2022", 11 pgs.

"U.S. Appl. No. 16/563,235, Response filed Nov. 16, 2021 to Non Final Office Action mailed Sep. 30, 2021", 13 pgs.

"U.S. Appl. No. 16/690,992, Advisory Action mailed Jul. 26, 2023", 3 pgs.

"U.S. Appl. No. 16/690,992, Final Office Action mailed May 15, 2023", 26 pgs.

"U.S. Appl. No. 16/690,992, Final Office Action mailed Jul. 26, 2022", 12 pgs.

"U.S. Appl. No. 16/690,992, Non Final Office Action mailed Feb. 6, 2023", 12 pgs.

"U.S. Appl. No. 16/690,992, Non Final Office Action mailed Apr. 5, 2022", 23 pgs.

"U.S. Appl. No. 16/690,992, Non Final Office Action mailed Aug. 24, 2023", 23 pgs.

"U.S. Appl. No. 16/690,992, Response filed Apr. 18, 2023 to Non Final Office Action mailed Feb. 6, 2023", 14 pgs.

"U.S. Appl. No. 16/690,992, Response filed Jul. 5, 2022 to Non Final Office Action mailed Apr. 5, 2022", 19 pgs.

"U.S. Appl. No. 16/690,992, Response filed Jul. 13, 2023 to Final Office Action mailed May 15, 2023", 19 pgs.

"U.S. Appl. No. 16/690,992, Response filed Oct. 26, 2022 to Final Office Action mailed Jul. 26, 2022", 12 pgs.

"U.S. Appl. No. 16/986,717, Final Office Action mailed Nov. 1, 2023", 16 pgs.

"U.S. Appl. No. 16/986,717, Non Final Office Action mailed May 31, 2023", 13 pgs.

"U.S. Appl. No. 16/986,717, Notice of Allowance mailed Feb. 2014, 24", 8 pgs.

"U.S. Appl. No. 16/986,717, Response filed Jan. 25, 2024 to Final Office Action mailed Nov. 1, 2023", 13 pgs.

(56)            References Cited

OTHER PUBLICATIONS

"U.S. Appl. No. 16/986,717, Response filed Apr. 19, 2023 to Restriction Requirement mailed Mar. 2, 2023", 8 pgs.

"U.S. Appl. No. 16/986,717, Response filed Aug. 9, 2023 to Non Final Office Action mailed May 31, 2023", 9 pgs.

"U.S. Appl. No. 16/986,717, Restriction Requirement mailed Mar. 2, 2023", 7 pgs.

"U.S. Appl. No. 17/329,765, Restriction Requirement mailed Sep. 13, 2023", 6 pgs.

"U.S. Appl. No. 17/329,795, Restriction Requirement mailed Sep. 13, 2023", 6 pgs.

"U.S. Appl. No. 17/329,823, Restriction Requirement mailed Sep. 13, 2023", 6 pgs.

"U.S. Appl. No. 17/329,842, Restriction Requirement mailed Oct. 17, 2023", 6 pgs.

"U.S. Appl. No. 18/144,368, Non Final Office Action mailed Apr. 12, 2024", 16 pgs.

"Chinese Application Serial No. 202080046425.X, Voluntary Amendment filed Jun. 14, 2022", w/ English Claims, 12 pgs.

"Chinese Application Serial No. 201380055918.X, Office Action mailed Jan. 17, 2018", (English Translation), 8 pgs.

"Chinese Application Serial No. 201380055918.X, Office Action mailed Feb. 19, 2019", W/ English Translation, 6 pgs.

"Chinese Application Serial No. 201380055918.X, Office Action mailed May 19, 2017", w/ English Translation, 18 pgs.

"Chinese Application Serial No. 201380055918.X, Office Action mailed Dec. 27, 2019", w/ English translation, 12 pgs.

"Chinese Application Serial No. 201380055918.X, Response filed Apr. 2, 2018 to Office Action mailed Jan. 17, 2018", w/ English claims, 15 pgs.

"Chinese Application Serial No. 201380055918.X, Response filed Aug. 23, 2019 to Office Action mailed Feb. 19, 2019", w/English Claims, 14 pgs.

"Chinese Application Serial No. 201380055918.X, Response filed Oct. 9, 2017 to Office Action mailed May 19, 2017", w/ English Claims, 16 pgs.

"Chinese Application Serial No. 201380055918.X, Response filed 11-27-8 to Office Action mailed", w/English Claims, 16 pgs.

"Chinese Application Serial No. 201580058938.1, Office Action mailed Jul. 2, 2020", w/ English translation, 14 pgs.

"Chinese Application Serial No. 201580058938.1, Office Action mailed Sep. 3, 2019", W/English Translation, 17 pgs.

"Chinese Application Serial No. 201580058938.1, Response filed Mar. 18, 2020 to Office Action mailed Sep. 3, 2019", w/English Claims, 15 pgs.

"Chinese Application Serial No. 201580058938.1, Response filed Nov. 24, 2020 to Office Action mailed Jul. 2, 2020", w/English Claims, 16 pgs.

"Chinese Application Serial No. 201580058938.1, Voluntary Amendment mailed Feb. 22, 2018", w/ English Claims, 21 pgs.

"Chinese Application Serial No. 201910917938.2, Decision of Rejection mailed Mar. 14, 2023", w/ English translation, 13 pgs.

"Chinese Application Serial No. 201910917938.2, Office Action mailed May 20, 2022", w/ English translation, 16 pgs.

"Chinese Application Serial No. 201910917938.2, Office Action mailed Oct. 18, 2022", w/ English translation, 7 pgs.

"Chinese Application Serial No. 201910917938.2, Response filed Feb. 27, 2023 to Office Action mailed Oct. 18, 2022", w/ English Claims, 8 pgs.

"Chinese Application Serial No. 201910917938.2, Response filed Jun. 28, 2023 to Decision of Rejection mailed Mar. 14, 2023", w/ English Claims, 13 pgs.

"Chinese Application Serial No. 201910917938.2, Response filed Sep. 28, 2022 to Office Action mailed May 20, 2022", w/ English Claims, 7 pgs.

"Chinese Application Serial No. 202110227749.X, Office Action mailed Dec. 22, 2023", w/ English Translation, 8 pgs.

"Chinese Application Serial No. 202110227749.X, Response filed May 6, 2024 to Office Action mailed Dec. 22, 2023", w/ current English claims, 15 pgs.

"Effectiveness and Safety of Bronchial Thermoplasty in the Treatment of Severe Asthma", A Multicenter, Randomized, Double-Blind, Sham-Controlled Clinical Trial Am J Respir Crit Care Med vol. 181., (2010), 9 pgs.

"European Application Serial No. 13851462.5, Communication Pursuant to Article 94(3) EPC mailed Mar. 20, 2020", 7 pgs.

"European Application Serial No. 13851462.5, Communication Pursuant to Article 94(3) EPC mailed Jun. 1, 2018", 9 pgs.

"European Application Serial No. 13851462.5, Extended European Search Report mailed Jun. 6, 2016", 6 pgs.

"European Application Serial No. 13851462.5, Invitation pursuant to Article 94(3) and Rule 71(1) EPC mailed Oct. 11, 2022", 4 pgs.

"European Application Serial No. 13851462.5, Office Action mailed Jun. 12, 2015", 3 pgs.

"European Application Serial No. 13851462.5, Response filed Jul. 20, 2020 to Communication Pursuant to Article 94(3) EPC mailed Mar. 20, 2020", 13 pgs.

"European Application Serial No. 13851462.5, Response filed Aug. 10, 2022 to Summons to Attend Oral Proceedings mailed Feb. 28, 2022", 52 pgs.

"European Application Serial No. 13851462.5, Response filed Oct. 19, 2015 to Office Action mailed Jun. 12, 2015", 13 pgs.

"European Application Serial No. 13851462.5, Response filed Dec. 1, 2016 to Extended European Search Report mailed Jun. 6, 2016", 20 pgs.

"European Application Serial No. 13851462.5, Summons to Attend Oral Proceedings mailed Jan. 28, 2022", 10 pgs.

"European Application Serial No. 13851462.5, Summons to Attend Oral Proceedings mailed Feb. 28, 2022", 4 pgs.

"European Application Serial No. 15853911.4, Communication Pursuant to Article 94(3) EPC mailed Apr. 28, 2022", 10 pgs.

"European Application Serial No. 15853911.4, Communication Pursuant to Article 94(3) EPC mailed Apr. 30, 2020", 8 pgs.

"European Application Serial No. 15853911.4, Extended European Search Report mailed May 30, 2018", 15 pgs.

"European Application Serial No. 15853911.4, Reponse filed Nov. 12, 2018 to Extended European Search Report mailed May 30, 2018", 17 pgs.

"European Application Serial No. 15853911.4, Response filed Sep. 2, 2022 to Communication Pursuant to Article 94(3) EPC mailed Apr. 28, 2022", 116 pgs.

"European Application Serial No. 15853911.4, Response filed Oct. 27, 2020 to Communication Pursuant to Article 94(3) EPC mailed Apr. 30, 2020", 14 pgs.

"European Application Serial No. 20832727.0, Extended European Search Report mailed Feb. 28, 2023", 9 pgs.

"European Application Serial No. 20832727.0, Response filed Sep. 26, 2023 to Communication pursuant to Rules 70(2) and 70a(2) EPC mailed Mar. 17, 2023", 15 pgs.

"European Application Serial No. 20832727.0, Response to Communication pursuant to Rules 161 and 162 filed Aug. 19, 2022", 13 pgs.

"European Application Serial No. 23183741.0, Extended European Search Report mailed Jul. 21, 2023", 14 pgs.

"European Application Serial No. 23183741.0, Response filed Feb. 19, 2024 to Extended European Search Report mailed Jul. 21, 2023", 12 pgs.

"International Application Serial No. PCT/US2015/058296, International Preliminary Report on Patentability mailed May 11, 2017", 9 pgs.

"International Application Serial No. PCT/US2020/039605, International Preliminary Report on Patentability mailed Jan. 6, 2022", 9 pgs.

"International Application Serial No. PCT/US2020/039605, International Search Report mailed Sep. 28, 2020", 2 pgs.

"International Application Serial No. PCT/US2020/039605, Written Opinion mailed Sep. 28, 2020", 7 pgs.

"International Application Serial No. PCT/US2022/050087, International Search Report mailed Mar. 1, 2023", 3 pgs.

"International Application Serial No. PCT/US2022/050087, Written Opinion mailed Mar. 1, 2023", 4 pgs.

"Japanese Application Serial No. 2015-540733, Office Action mailed Jul. 4, 2017", w/English Translation, 12 pgs.

(56) References Cited

OTHER PUBLICATIONS

"Japanese Application Serial No. 2015-540733, Office Action mailed Dec. 29, 2017", With English Translation, 9 pgs.

"Japanese Application Serial No. 2015-540733, Response filed Mar. 16, 2018 to Office Action mailed Dec. 29, 2017", w/ English Claims, 11 pgs.

"Japanese Application Serial No. 2015-540733, Response filed Oct. 4, 2017 to Office Action mailed Jul. 4, 2017", w/ English Claims, 19 pgs.

"Japanese Application Serial No. 2017-523517, Notification of Reasons for Refusal mailed Jul. 6, 2021", w/ English Translation, 9 pgs.

"Japanese Application Serial No. 2017-523517, Notification of Reasons for Rejection mailed Sep. 10, 2019", w/ English Translation, 13 pgs.

"Japanese Application Serial No. 2017-523517, Office Action mailed Jun. 23, 2020", w/ English translation, 14 pgs.

"Japanese Application Serial No. 2017-523517, Response filed Mar. 6, 2020 to Notification of Reasons for Rejection mailed Sep. 10, 2019", w/English Claims, 14 pgs.

"Japanese Application Serial No. 2017-523517, Response filed Oct. 23, 2020 to Office Action mailed Jun. 23, 2020", w/English Claims, 14 pgs.

"Japanese Application Serial No. 2018-153239, Examiners Decision of Final Refusal mailed Apr. 7, 2020", w/ English Translation, 9 pgs.

"Japanese Application Serial No. 2018-153239, Notification of Reasons for Refusal mailed Jan. 5, 2022", w/ English Translation, 17 pgs.

"Japanese Application Serial No. 2018-153239, Notification of Reasons for Refusal mailed Jul. 2, 2019", W/ English Translation, 16 pgs.

"Japanese Application Serial No. 2018-153239, Notification of Reasons for Refusal mailed Aug. 17, 2021", w/ English Translation, 17 pgs.

"Japanese Application Serial No. 2018-153239, Office Action mailed Nov. 8, 2022", w/ English Translation, 45 pgs.

"Japanese Application Serial No. 2018-153239, Response filed Apr. 5, 2022 to Notification of Reasons for Refusal mailed Jan. 5, 2022", w/ English Claims, 9 pgs.

"Japanese Application Serial No. 2018-153239, Response filed Oct. 1, 2019 to Notification of Reasons for Refusal mailed Jul. 2, 2019", w/English Claims, 10 pgs.

"Japanese Application Serial No. 2018-153239, Response filed Nov. 16, 2021 to Notification of Reasons for Refusal mailed Aug. 17, 2021", w/Engilsh Claims, 10 pgs.

"Japanese Application Serial No. 2020-134047, Examiners Decision of Final Refusal mailed Jun. 21, 2022", w/ English translation, 6 pgs.

"Japanese Application Serial No. 2020-134047, Notification of Reasons for Refusal mailed Sep. 28, 2021", w/ English Translation, 16 pgs.

"Japanese Application Serial No. 2020-134047, Response filed Mar. 28, 2022 to Notification of Reasons for Refusal mailed Sep. 28, 2021", w/ English translation, 21 pgs.

"Japanese Application Serial No. 2020-178075, Notification of Reasons for Refusal mailed Jan. 5, 2022", w/ English Translation, 8 pgs.

"Japanese Application Serial No. 2020-178075, Office Action mailed Nov. 22, 2022", w/o English Translation, 1 pg.

"Japanese Application Serial No. 2020-178075, Preliminary Examination Report mailed Jan. 24, 2023", w/ English Translation, 2 pgs.

"Japanese Application Serial No. 2020-178075, Response field Dec. 21, 2022 to Office Action mailed Nov. 22, 2022", w/English Translation, 11 pgs.

"Japanese Application Serial No. 2020-178075, Response filed Apr. 5, 2022 to Notification of Reasons for Refusal mailed Jan. 5, 2022", w English translation, 6 pgs.

"Japanese Application Serial No. 202080044525.9, Examiners Decision of Final Refusal mailed Jul. 5, 2022", w/ English Translation, 8 pgs.

"Japanese Application Serial No. 202080044525.9, Response filed Nov. 7, 2022 to Examiners Decision of Final Refusal mailed Jul. 5, 2022", w/ English Claims, 13 pgs.

"Japanese Application Serial No. 2022-169101, Notification of Reasons for Rejection mailed Oct. 31, 2023", W/ English Translation, 9 pgs.

"Japanese Application Serial No. 2022-169101, Response filed Jan. 30, 2024 to Notification of Reasons for Rejection mailed Oct. 31, 2023", w/ English Claims, 14 pgs.

"Japanese Application Serial No. 2022-169101, Voluntary Amendment filed Jun. 19, 2023", 15 pgs.

"Japanese Application Serial No. 2022-178135, Notification of Reasons for Refusal mailed Nov. 11, 2023", w/ English Translation, 10 pgs.

"Japanese Application Serial No. 2022-178135, Response filed Feb. 27, 2024 to Notification of Reasons for Refusal mailed Nov. 11, 2023", w/ english claims, 9 pgs.

Dunican, Eleanor M, "Mucus plugs in patients with asthma linked to eosinophilia and airflow obstruction", J Clin Invest. 2018;128(3), (2018), 14 pgs.

Greer, M, et al., "Paclitaxel-Coated Balloons in Refractory Nonanastomostic Airway Stenosis Following Lung Transplantation", American Journal of Transplantation 2014 14: 2400-2405, (2014), 2400-2405.

Kim, K. C., et al., "Airway goblet cell mucin: its structure and regulation of secretion", Series Airway Mucus Eur Respir J 1997; 10:, (1997), pp. 2644-2649.

Krmisky, William, et al., "Thermal ablation for asthma: current status and technique", J Thorac Dis 2017;9(Suppl 2):S104-S109, (2017), 6 pgs.

Krum, H., et al., "Catheter-based renal sympathetic denervation for resistant hypertension: a multicentre safety and proof-of-principle cohort study.", Lancet, 373(9671), (2009), 2375-1281.

Menzella, Francesco, et al., "Anti-IL5 Therapies for Severe Eosinophilic Asthma: Literature Review and Practical Insights", Journal of Asthma and Allergy 2020:13, (2020), 13 pgs.

Peters, Michael C, et al., "Evidence for Exacerbation-Prone Asthma and Predictive Biomarkers of Exacerbation Frequency", Am J Respir Crit Care Med vol. 202, Iss 7, (2020), 10 pgs.

Sakata, Kenneth K, et al., "Paclitaxel-coated balloon dilation for central airway obstruction", Respiratory Medicine Case Reports 24, (2018), 129-132.

Tian, Juanhua, et al., "Rectifying disorder of extracellularmatrix to suppress urethral stricture by protein nanofilm-controlled drug delivery from urinary catheter", nature communications, (May 17, 2023), 17 pgs.

"Chinese Application Serial No. 202080046425.X, 2024075838, Response filed May 20, 2025 to Office Action mailed Mar. 20, 2025", W English Claims, 11 pgs.

"U.S. Appl. No. 17/610,472, Restriction Requirement mailed May 22, 2025", 7 pgs.

"Japanese Application Serial No. 2022-178135, Response filed May 2, 2025 to Final Notification of Reasons for Rejection mailed Jan. 7, 2025", w english claims, 23 pgs.

"Response to Examiner Telephone Interview filed Jun. 3, 2025", w english claims, 10 pgs.

"Chinese Application Serial No. 202080046425.X, Office Action mailed Mar. 20, 2025", w English translation, 4 pgs.

"Japanese Application Serial No. 2021-576638, Response filed Mar. 27, 2025 to Notification of Reasons for Rejection mailed Jan. 7, 2025", w english claims, 22 pgs.

"Japanese Application Serial No. 2025-076723, Voluntary Amendment filed May 27, 2025", w english claim, 8 pgs.

"U.S. Appl. No. 17/719,032, Restriction Requirement mailed Jun. 10, 2025", 5 pgs.

"U.S. Appl. No. 17/610,472, Advisory Action mailed Dec. 16, 2025", 3 pgs.

"U.S. Appl. No. 17/610,472, Final Office Action mailed Oct. 27, 2025", 7 pgs.

(56)        References Cited

OTHER PUBLICATIONS

"U.S. Appl. No. 17/610,472, Non Final Office Action mailed Aug. 4, 2025", 10 pgs.

"U.S. Appl. No. 17/610,472, Response filed Jul. 14, 2025 to Restriction Requirement mailed May 22, 2025", 9 pgs.

"U.S. Appl. No. 17/610,472, Response filed Oct. 14, 2025 to Non Final Office Action mailed Aug. 4, 2025", 13 pgs.

"U.S. Appl. No. 17/610,472, Response filed Dec. 9, 2025 to Final Office Action mailed Oct. 27, 2025", 14 pgs.

"U.S. Appl. No. 17/719,032, Non Final Office Action mailed Sep. 24, 2025", 9 pgs.

"U.S. Appl. No. 17/719,032, Response filed Jul. 16, 2025 to Restriction Requirement mailed Jun. 10, 2025", 8 pgs.

"U.S. Appl. No. 17/719,032, Response filed Nov. 12, 2025 to Non Final Office Action mailed Sep. 24, 2025", 8 pgs.

"U.S. Appl. No. 19/281,082, Non Final Office Action mailed Nov. 5, 2025", 15 pgs.

"European Application Serial No. 15853911.4, Communication Pursuant to Article 94(3) EPC mailed Jul. 14, 2025", 7 pgs.

"European Application Serial No. 15853911.4, Response filed Nov. 11, 2025 to Communication Pursuant to Article 94(3) EPC mailed Jul. 14, 2025", 119 pgs.

"European Application Serial No. 20832727.0, Communication Pursuant to Article 94(3) EPC mailed Jul. 31, 2025", 5 pgs.

"European Application Serial No. 20832727.0, Response filed Nov. 28, 2025 to Communication Pursuant to Article 94(3) EPC mailed Jul. 31, 2025", w/ English Claims, 14 pgs.

"European Application Serial No. 22826521.1, Communication Pursuant to Article 94(3) EPC mailed Nov. 26, 2025", 5 pgs.

"European Application Serial No. 24205384.1, Response filed Jul. 11, 2025 to Extended European Search Report mailed Dec. 12, 2024", w/ claims, 13 pgs.

"Japanese Application Serial No. 2024-158261, Notification of Reasons for Refusal mailed Nov. 4, 2025", W/ English Translation, 8 pgs.

"Japanese Application Serial No. 2025-127352, Amendment filed Sep. 2, 2025", w/ English Machine Translation, 4 pgs.

Chen, Shao-Liang, et al., "Pulmonary artery denervation to treat pulmonary arterial hypertension: The single-center, prospective, first-in-man PADN-1 study", Journal of the American College of Cardiology (2013), doi: 10.1016/j.jacc.2013.05.075., Accepted Manuscript, (2013), 9 pgs.

Lee, Hyeog Jong, et al., "Chemical Ablation of the Gallbladder with Acetic Acid", J Vase Interv Radiol, (2009), 6 pgs.

"U.S. Appl. No. 17/610,472, Non Final Office Action mailed Feb. 26, 2026", 11 pgs.

"U.S. Appl. No. 17/719,032, Response filed Feb. 16, 2026 to Final Office Action mailed Jan. 16, 2026", 9 pgs.

"U.S. Appl. No. 18/644,498, Non Final Office Action mailed Feb. 3, 2026", 16 pgs.

"U.S. Appl. No. 18/644,542, Non Final Office Action mailed Feb. 12, 2026", 22 pgs.

"U.S. Appl. No. 19/281,082, Final Office Action mailed Mar. 4, 2026", 19 pgs.

"European Application Serial No. 22826521.1, Response filed Mar. 3, 2026 to Communication Pursuant to Article 94(3) EPC mailed Nov. 26, 2025", W/ English Claims, 21 pgs.

"Japanese Application Serial No. 2024-158261, Response filed Feb. 4, 2026 to Notification of Reasons for Refusal mailed Nov. 4, 2025", w/ English Claims, 13 pgs.

Jonge, Charlotte De, et al., "Endoscopic Duodenal-Jejunal Bypass Liner Rapidly Improves Type 2 Diabetes", Obesity Surgery, [Online]. Retrieved from the Internet: <https://pubmed.ncbi.nlm.nih.gov/23526068/>, (2013), 1354-1360.

Matthes, Kai, et al., "Concentration-dependent ablation of pancreatic tissue by EUS-guided ethanol injection", Gastrointestinal Endoscopy, [Online]. Retrieved from the Internet: <https://www.sciencedirect.com/science/article/pii/S0016510706019195>, (2007), 6 pages.

Sikaris, Ken, et al., "The Correlation of Hemoglobin A1c to Blood Glucose", Journal of Diabetes Science and Technology, vol. 3, Issue 3, (May 2009), 429-438.

"U.S. Appl. No. 17/719,032, Notice of Allowance mailed Mar. 24, 2026", 7 pgs.

"U.S. Appl. No. 18/644,498, Response filed Mar. 27, 2026 to Non Final Office Action mailed Feb. 3, 2026", 17 pgs.

"U.S. Appl. No. 17/610,472, Response filed Mar. 27, 2026 to Non Final Office Action mailed Feb. 26, 2026", 16 pgs.

"U.S. Appl. No. 18/644,542, Response filed Mar. 27, 2026 to Non Final Office Action mailed Feb. 12, 2026", 15 pgs.

"Japanese Application Serial No. 2024-556034, Voluntary Amendment Filed Nov. 5, 2025", w English Claims, 11 pgs.

"U.S. Appl. No. 18/955,026, Non Final Office Action mailed Jan. 16, 2026", 21 pgs.

"U.S. Appl. No. 17/719,832, Final Office Action mailed Jan. 16, 2026", 9 pgs.

"U.S. Appl. No. 19/281,082, Response filed Jan. 23, 2026 to Non Final Office Action mailed Nov. 5, 2025", 19 pgs.

* cited by examiner

FIG. 4A            FIG. 4B

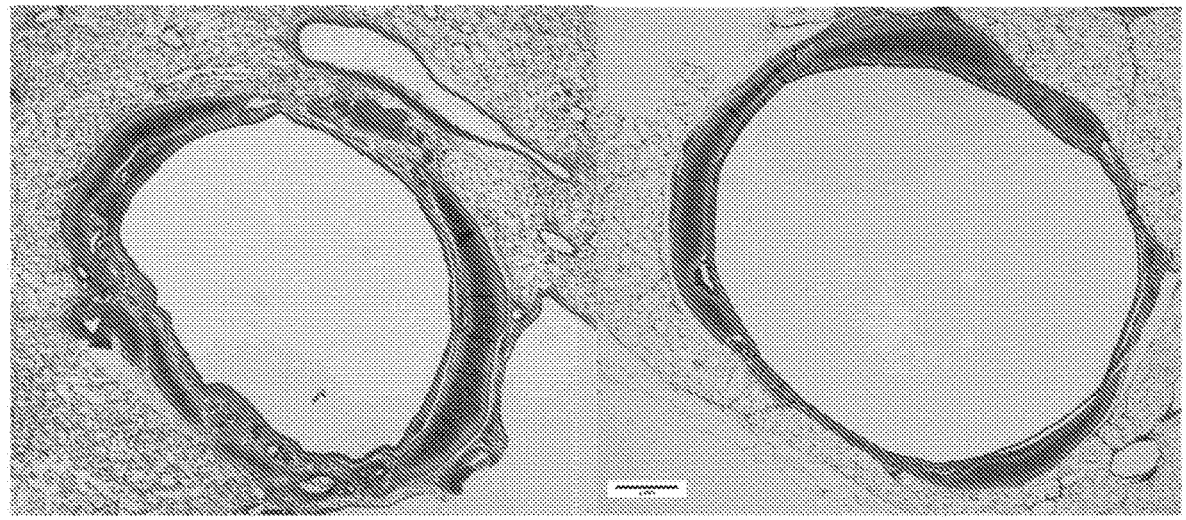
FIG. 8A                    FIG. 8B

METHOD FOR TREATMENT OF AIRWAY STRICTURE OR STENOSIS

CROSS-REFERENCE TO RELATED APPLICATION

This application is a U.S. National Stage Application under 35 U.S.C. 371 from International Application No. PCT/US2022/050087, filed Nov. 16, 2022, and published as WO 2023/091475 on May 25, 2023, which claims the benefit of priority to U.S. Provisional Patent Application Ser. No. 63/279,776 filed Nov. 16, 2021, the disclosure of which are incorporated herein in their entirety by reference.

BACKGROUND

Chronic rhinosinusitis (CRS) is an inflammation of the membrane lining of one or more paranasal sinuses. Chronic rhinosinusitis lasts longer than three weeks and often continues for months. In cases of chronic rhinosinusitis, there is usually tissue damage. According to the Center for Disease Control, thirty-seven million cases of chronic sinusitis are reported annually.

Chronic rhinosinusitis (CRS) is widely thought to be a common disease—many studies cite a prevalence of 10-15% (see, e.g., Adam S. DeConde et al., Am J Rhinol Allergy 30, 134-139, 2016). Chronic rhinosinusitis with Nasal Polyps (CRSwNP) and Nasal Polyps (NP) is about 25-30% of CRS. CRSwNP is an inflammatory condition of the nose and paranasal sinuses of unknown cause which is present in 2%-4% of the adult population. In the USA, the direct costs for the management of CRS are now between $10 and $13 billion per year, or about $2.6K per patient per year. The highest direct costs were associated with patients who had recurrent polyposis after surgery. The surgery is expensive, varying from up to $11,000 in USA (EPOS 2020). Surgery and medication are recommended for difficult-to-treat CRS (patients who have persistent symptoms of CRS despite appropriate treatment). Recurrence of CRSwNP after surgery is common and occurs in as many as 60% of patients (50% of these patients have had previous surgery) (see, Adam S. DeConde et al., Am J Rhinol Allergy 30, 134-139, 2016).

Asthma is a chronic respiratory disease characterized by inflammation of the airways, excess mucus production, airway hyper-responsiveness, and a condition in which airways narrow excessively or too easily respond to a stimulus. Asthma episodes or attacks cause narrowing of the airways via smooth muscle contractions in the airways, which makes breathing difficult. Asthma attacks can have a significant impact on a patient's life and can limit participation in many activities. In severe cases, asthma attacks can be life-threatening. Of the more than 35 million people in the U.S. living with asthma, about 5-10% suffer from severe asthma. Presently, there is no known cure for asthma.

CRS is associated with asthma, with a prevalence of asthma around 25% in patients with CRS compared to 5% in the general population. Patients with chronic rhinosinusitis with nasal polyps (CRSwNP) often have coexisting asthma under the concept of "United Airway Disease", being the combination of both diseases, which is one of the most challenging disease to treat. The effect of CRSwNP treatment, whether medical or surgical, in asthma is today less controversial after some studies have shown improvement of asthma after medical and/or surgical treatment of CRSwNP.

Chronic obstructive pulmonary disease (COPD) is a term used to classify two major airflow obstruction disorders: chronic bronchitis and emphysema. Approximately 16 million Americans have COPD, with about 80-90% of them smokers throughout much of their lives. COPD is a leading cause of death in the U.S. Chronic bronchitis is inflammation of the bronchial airways. The bronchial airways connect the trachea with the lungs. When inflamed, the bronchial tubes secrete mucus, causing a chronic cough. Emphysema is an over-inflation of the alveoli, or air sacs in the lungs. This condition causes shortness of breath.

Mucus can accumulate in the lungs and can plug up the airway, reducing air flow. Airway plugs can include viscous high molecular weight glycoproteins. These proteins are over-produced by goblet cells and submucosal glands in the airway tracts of the lungs. If the mucus plugs are in the larger upper airways, such as mainstem bronchus, *bronchus intermedius*, or a lobar bronchus, this condition can lead to a shortness of breath or death of the patients as seen in chronic bronchitis, asthma, and cystic fibrosis.

The uncontrolled localized production of IL-5, IL-6, IL-4, IL-13, IL-23, and/or ILC2 in the airway can contribute to airway eosinophilia in patients with severe eosinophilic asthma. IL-5, IL-6, IL-4, IL-13, IL-23, eosinophils, and other targeted cells in airway can be responsible for airway inflammation in asthmatics. Various humanized monoclonal antibodies have been developed to target these cells to treat severe asthma. These biological medicines require continued administration yearly or throughout the patient's life, with the disease reoccurring upon cessation of treatment.

Airway restenosis is one of the challenging pathologies to treat in the field of otorhinolaryngology and pulmonology. It can be at the level of supraglottis, glottis, subglottis, trachea, mainstem bronchus, *bronchus intermedius*, or a lobar bronchus. Of the wide range of etiologies, e.g., congenital, traumatic, inflammatory, and idiopathic, trauma following prolonged intubation and tracheostomy is still considered the commonest cause for the development of airway stenosis in both pediatric and adult population. Benign strictures or restenosis constitute most benign forms of airway restenosis and include airway restenosis related to post-intubation tracheal stenosis, post-tracheostomy tracheal restenosis, post-tuberculosis infection, transplant-related, and idiopathic restenosis. There are various methods for alleviating symptoms in patients with airway restenosis, which include mechanical debulking, rigid bronchoscopic dilation, stent placement, and balloon dilation. These treatments can be used to provide relief of the stenotic or strictured airway segment, though the stenosis often recurs and then repeated treatments are needed.

SUMMARY OF THE INVENTION

The present invention provides a method of treatment of a recurring airway stricture or stenosis in an airway body lumen. The method includes inserting a scope and a balloon catheter into the target site at the recurring airway stricture of stenosis in the airway body lumen. The balloon catheter includes an elongated balloon. The balloon catheter also includes a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site.

The present invention provides a method of treatment of a recurring airway stricture or stenosis in an airway body lumen. The method includes damaging, dilating, and/or removing the stricture or stenosis at a target site in the body lumen. The method includes flushing the target site with a flushing composition including water and/or saline. The method includes inserting a scope and a balloon catheter into the target site. The balloon catheter includes an elongated balloon. The balloon catheter also includes a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes hydrating and/or soaking the coating in the flushing composition at the target site. The method includes inflating the balloon to an inflation diameter such that the coating contacts an interior of the body lumen at the target site. The method includes deflating the balloon. The method also includes withdrawing the scope and the balloon catheter from the target site. Prior to inflation the coating on the drug coated balloon is hydrated and/or soaked to activate the coating.

The present invention provides a method of treatment of chronic rhinosinusitis with nasal polyps (CRSwNP). The method includes removing at least one of the nasal polyps at a target site in the body lumen. The method includes inserting a scope and a balloon catheter into the target site in a body lumen. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. Prior to inflation the coating on the drug coated balloon is hydrated and/or soaked to activate the coating.

The present invention provides a method of treatment of laryngostenosis and/or subglottic stricture or stenosis. The method includes damaging, dilating, and/or removing the laryngostenosis and/or subglottic stricture or stenosis at a target site in the body lumen. The method includes inserting a scope and a balloon catheter into the target site in a body lumen. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. Prior to inflation the coating on the drug coated balloon is hydrated and/or soaked to activate the coating.

The present invention provides a method of treatment of severe asthma. The method includes inserting a scope and a balloon catheter into a target site in a body lumen including a trachea, mainstem bronchus, *bronchus intermedius*, and/or a lobar bronchus. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. The method can include treating more than one treatment site. The method can include at least one drug-coated balloon catheter, two drug-coated balloon catheters, or more than two drug-coated balloon catheters. In embodiments that include treating more than one treatment site, the treatments can be performed sequentially or a time delay can occur between the treatments, such as a time delay of 1 to 6 weeks. For example, in one embodiment, bronchi in the upper lung can be treated in a first treatment, and untreated bronchi in a different part of the lung can be treated in a later (e.g., second) treatment. Asthma episodes or attacks can cause narrowing of the airways by smooth muscle contractions in the airways. In various embodiments, the drug released from the drug-coated balloon can reduce the amount of smooth muscle cells in the airway, such as by 5% to 50%. Prior to inflation the coating on the drug coated balloon is hydrated and/or soaked to activate the coating.

The present invention provides a method of reduction of exacerbation of and/or hospitalization for severe asthma. The method includes inserting a scope and a balloon catheter into a target site in a body lumen including a trachea, mainstem bronchus, *bronchus intermedius*, and/or a lobar bronchus. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. In various embodiments, the drug released from the drug-coated balloon can reduce the concentration of smooth muscle cells in the airway, such as by 5% to 50%, leading to reduction of exacerbation of and/or hospitalization for severe asthma and less smooth muscle contractions in the airway. Prior to inflation the coating on the drug coated balloon is hydrated and/or soaked to activate the coating.

The present invention provides a method of reducing a concentration of bronchial smooth muscle cells of a severe asthma patient. The method includes inserting a scope and a balloon catheter into a target site including bronchial smooth muscle cells in a body lumen. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. Prior to inflation the coating on the drug coated balloon is hydrated and/or soaked to activate the coating.

The present invention provides a method of treatment of chronic rhinosinusitis with nasal polyps (CRSwNP) and asthma. The method includes removing at least one of the nasal polyps at a first target site in a first body lumen. The method includes inserting a first scope and a first balloon catheter into the first target site in the first body lumen. The first balloon catheter includes a first elongated balloon. The first balloon catheter also includes a first coating layer overlying an exterior surface of the first balloon. The first coating layer includes one or more first additives and an initial drug load of a first therapeutic agent chosen from paclitaxel, docetaxel, taxol, rapamycin, sirolimus, zotarolimus, everolimus, tacrolimus, an analogue thereof, and a combination thereof. The method includes inflating the first balloon to a first inflation diameter such that the first coating layer contacts an interior of the first body lumen at the first target site. The method includes deflating the first balloon. The method includes withdrawing the first scope and the first balloon catheter from the first target site. The method includes inserting a second scope and a second balloon catheter into a second target site in a second body lumen including a trachea and/or a bronchus. The second balloon catheter includes a second elongated balloon. The second balloon catheter also includes a second coating layer overlying an exterior surface of the second balloon. The second coating layer includes one or more second additives and an initial drug load of a second therapeutic agent chosen from paclitaxel, docetaxel, taxol, rapamycin, sirolimus, zotarolimus, everolimus, tacrolimus, an analogue thereof, and a combination thereof. The method includes inflating the second balloon to an inflation diameter such that the coating contacts an interior of the second body lumen at the second target site. The method includes deflating the second balloon. The method also includes withdrawing the second scope and the second balloon catheter from the second target site. In various embodiments, the second target site includes a bronchus, such as a mainstem bronchus, *bronchus intermedius*, and/or a lobar bronchus. In various embodiments, the asthma is severe asthma. In various embodiments, treating CRSwNP and asthma simultaneously can advantageously cause synergism with greater total treatment effect that the combined total treatment effect of treating CRSwNP and asthma independently. Prior to inflation the coating on the first and/or second drug coated balloon is hydrated and/or soaked to activate the coating.

The present invention provides a method of reducing a concentration of eosinophils, IL-4, IL-5, IL-6, IL-13, IL-23, and/or ILC2 in an airway tract, such as in severe asthma patients. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method also includes withdrawing the scope and the balloon catheter from the target site. Prior to inflating the coating on the drug coated balloon is hydrated and/or soaked to activate the coating.

The present invention provides a method of treatment of a mucous plug in an airway. The method can optionally include removing the mucous plug. The method includes inserting a scope and a balloon catheter into a target site that included a mucous plug in an airway body lumen. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. In various embodiments, the drug released from the drug-coated balloon can reduce the concentration of goblet cells in the airway, preventing or reducing production of viscous mucous plugs in the airway. Prior to inflation the coating on the drug coated balloon is hydrated and/or soaked to activate the coating.

The present invention provides a method of reduction of concentration of goblet cells in an airway tract. The method includes inserting a scope and a balloon catheter into a target site including one or more goblet cells in a body lumen. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. The drug released from the drug coated balloon can reduce the concentration of goblet cells in the airway. Prior to inflation the coating on the drug coated balloon is hydrated and/or soaked to activate the coating.

The present invention provides a method of reducing a concentration of one or more mucins in the airway tract. Mucins are gel-forming glycoproteins in mucous plugs. Mucins are produced by mucous overproduction and hypersecretion in chronically inflamed airways. The method includes inserting a scope and a balloon catheter into a target site in a body lumen including a trachea, mainstem bronchus, *bronchus intermedius*, and/or a lobar bronchus. The balloon catheter includes an elongated balloon and a coating layer overlying an exterior surface of the balloon. The coating layer includes one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method includes inflating the balloon to an inflation diameter such that the coating contacts an interior of the body lumen at the target site. The method includes deflating the balloon. The method also includes withdrawing the scope and the balloon catheter from the target site. Prior to inflation the coating on the drug coated balloon is hydrated and/or soaked to activate the coating.

In various embodiments, the present invention provides a minimally invasive method for treatment or prevention of recuring stricture or stenosis of the frontal sinus, ethmoid sinus, sphenoid sinus, maxillary sinus, nasal passage, supraglottis, glottis, subglottis, trachea, mainstem bronchus, *bron-*

*chus intermedius*, or a lobar bronchus. The method includes inserting a catheter with an expandable body through the body lumen that contains the recurring stricture or stenosis such that the expandable body is inside the stricture or stenosis. The catheter with an expandable body can include a balloon catheter, a drug coated catheter, a drug eluting stent, and/or a drug eluting stent crimped on a drug coated balloon. The catheter includes an expandable body with a coating layer, or more than one layer, containing a therapeutic agent and one more additives overlying the exterior surface of the expandable body of the catheter. The one or more additives are chosen from one or more water insoluble additives, slightly water insoluble additives, partially water soluble additives, water soluble additives, or a combination thereof. The method includes expanding the body to contact the coating layer with the stricture or stenosis in the body lumen to a certain diameter for a period of time. The method includes contracting the expanded body after the time period and withdrawing the catheter from the treated stricture or stenosis. In some embodiments, the method further includes performing a surgical procedure to dilate, cut, or remove tissue prior to the insertion of the balloon catheter into the target site. Prior to inflation the coating on the drug coated balloon is hydrated and/or soaked to activate the coating.

Embodiments of the present invention provide a medical device coating formulation including a therapeutic agent or drug for treatment of the strictures or stenosis in airway body lumens, and additives that enhance absorption of the drug into tissue of body lumens. Some embodiments provide a coating that overlays the expandable portion of the catheter that has a single layer or multiple layers that contain a single or multiple therapeutic agent. In some embodiments the layer in contact with the expandable portion of the catheter has no therapeutic agent and is formulated with ingredients that allow the entire or a substantial portion of the coating to transfer to the stricture or stenosis upon expansion of the catheter. Causes of the stricture or stenosis can include infections and inflammations by pathogens such as bacteria and viruses. In some embodiments the coating has additives that have antibacterial and antiviral properties. In some embodiments the layer of coating that contains the therapeutic agent includes drug that is crystalline, amorphous, or a combination thereof. In some embodiments the layer of coating that contains the therapeutic agent has at least one hydrophilic ingredient and at least one hydrophobic ingredient. In some embodiments the coating layers contain ingredients that enhance the adhesion of the coating with the luminal surface of the dilated stricture or stenosis. In some embodiments the coating is formulated such that upon expansion of the catheter the coating transfers to the stricture or stenosis as a particulate, agglomerated particulate, dissolved matter, or a combination thereof. In some embodiments the size of the particulate or agglomerated particulate transferred is small and less than 10 μm, or more preferably less than 5 μm.

In various embodiments, the present invention provides a catheter including an expandable portion of an elongated body that is used to dilate recuring airway strictures or restenosis. In some embodiments the elongated body is a balloon with a cylindrical shape. In some embodiments the elongated body is a balloon that has a shape or longitudinal profile that prevents migration of the balloon in the body lumen it is expanded in.

Embodiments of the present invention relate to balloon catheters having a rapid drug-releasing coating and methods for using the same to treat airway strictures or stenosis. The therapeutic agent according to embodiments of the present invention does not require a delayed or long-term release; rather, the therapeutic agent and the additive are released in a short time period to provide a rapid therapeutic effect. An object of embodiments of the present invention is to facilitate rapid and efficient uptake of drug by target tissue during transitory device deployment at a target site.

Various conventional treatments for severe asthma or chronic rhinosinusitis with nasal polyps (CRSwNP) require yearly retreatments or continued retreatments throughout a patient's life to avoid recurrence of the treated condition. However, in various embodiments of the present invention, the method can be effective to avoid recurrence of the treated condition, such as for the patient's entire life, or for 3 years, 5 years, or 10 years.

BRIEF DESCRIPTION OF THE FIGURES

The drawings illustrate generally, by way of example, but not by way of limitation, various embodiments of the present invention.

FIGS. 4A-4C are cross-sectional views of different embodiments of the distal portion of the balloon catheter of FIG. 3, taken along line A-A, showing exemplary coating layers, in accordance with various embodiments.

FIG. 8A illustrates a test article treatment site 28 days after treatment, in accordance with various embodiments.

FIG. 8B illustrates a control article treatment site after 28 days, in accordance with various embodiments.

DETAILED DESCRIPTION OF THE INVENTION

Figure 1A:
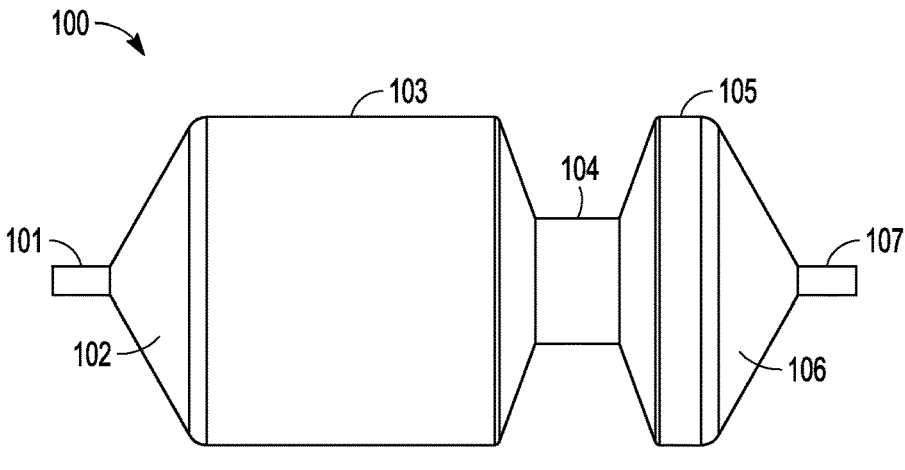
FIG. 1A illustrates a balloon catheter having one neck section, in accordance with various embodiments.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in a specific order as recited herein. Alternatively, in any aspect(s) disclosed herein, specific acts may be carried out in any order without departing from the principles of the invention, except when a temporal or operational sequence is explicitly recited. Furthermore, specified acts can be carried out concurrently unless explicit claim language recites that they be carried out separately or the plain meaning of the claims would require it. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of a material present does not affect the material properties of the composition including the material, such that about 0 wt % to about 5 wt % of the composition is the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

Method of Treatment of a Recurring Airway Stricture or Stenosis in an Airway Body Lumen.

The present invention provides a method of treatment of a recurring airway stricture or stenosis in an airway body lumen. The method can open the body lumen and can prevent, reduce, or minimize re-narrowing and recurring strictures or restenosis of the body lumen. The method can prevent recurrence of the stricture or stenosis, or can cause recurrence to be less frequent and/or can cause recurrence to be less severe as compared to conventional treatments. The treatment can be performed on a variety of animals and humans, such as premature neonates to adult humans. In various embodiments, the present invention provides a minimally invasive method for treatment or prevention of recurring strictures of the upper and lower airways.

The body lumen can be any suitable airway body lumen that includes a stricture or stenosis that has recurred at least one time. The body lumen can include a frontal sinus, ethmoid sinus, sphenoid sinus, maxillary sinus, nasal passage, supraglottis, glottis, subglottis, trachea, mainstem bronchus, *bronchus intermedius*, and/or a lobar bronchus.

The recurring stricture or stenosis can be caused by any suitable condition. The recurring stricture or stenosis can be idiopathic. The recurring stricture or stenosis can be caused by a surgical treatment. The recurring stricture or stenosis can be caused by a congenital condition, trauma, inflammation, post-intubation tracheal stenosis, post-tracheostomy tracheal restenosis, post-tuberculosis infection, transplant-related restenosis, repeated medication treatments, surgical removal, electrocautery, laser ablation, cryoablation, mechanical debulking, rigid bronchoscopic dilation, stent placement, and/or balloon dilation. The recurring stricture or stenosis can be caused by bronchial smooth muscle cells, IL-4, IL-5, IL-6, IL-13, IL-23, ILC2, mucus plug, goblet cells, fibrosis, cystic fibrosis, and/or one or more mucins. The stricture or stenosis can include CRS stenosis, CRSwNP stenosis, nasal stenosis, severe asthma, comorbidities of CRSwNP, comorbidities of severe asthma stenosis, subglottic stricture and/or stenosis, laryngostenosis, tracheal stenosis, bronchial stenosis, airway anastomotic stenosis, and/or radiation induced airway stenosis. In the treatment of severe asthma, the method can reduce or weaken the smooth muscles in the wall of treated bronchial airways to prevent or reduce recurrence of the severe asthma. In various embodiments, the method can include treating CRSwNP and severe asthma in one procedure, including treating at least two of the trachea, mainstem bronchus, *bronchus intermedius*, or a lobar bronchus. CRSwNP and severe asthma can be comorbidities and treating one can benefit the other. The treatment of CRSwNP can reduce or eliminate recurrence of the severe asthma, and vice versa.

The airway stricture or stenosis can include chronic rhinosinusitis with nasal polyps (CRSwNP). The airway stricture or stenosis can include laryngostenosis and/or subglottic stricture or stenosis. The airway stricture or stenosis can be a stricture or stenosis induced by repeated medication treatments, intubation, tracheostomy, tuberculosis infection, surgical removal, electrocautery, laser ablation, cryoablation, mechanical debulking, rigid bronchoscopic dilation, stent placement, and/or balloon dilation.

The method can include hydrating and/or soaking the coating prior to inflation of the drug-coated balloon. The hydrating and/or soaking can be performed outside the body (e.g., using saline, water, or a combination thereof), during passage to the target site while in the body lumen, at the target site, or a combination thereof. Hydrating and/or soaking that occurs during passage to the target site while in the body lumen, or that occurs at the target site, can include hydrating and/or soaking with flushing composition, natural fluids native to the body lumen that are not externally added, or a combination thereof. In various aspects, for treatment of pulmonary tissue, the method can include pre-soaking the coating prior to insertion to the target site. In various aspects, for treatment of nasal tissue or other non-pulmonary tissue, the method can include pre-soaking the coating prior to insertion to the target site, flushing the target site prior to insertion of the drug-coated balloon to the target site, or a combination thereof.

The method can include flushing the target site with a flushing composition including water and/or saline. The method can include inserting a scope and a balloon catheter into the target site. The flushing can be performed before and/or during the inserting of the scope and balloon catheter into the target site. The balloon catheter can include an elongated balloon. The balloon catheter can also include a coating layer overlying an exterior surface of the balloon. The coating layer can include one or more additives and an initial drug load of a therapeutic agent chosen from paclitaxel, docetaxel, taxol, rapamycin, sirolimus, zotarolimus, everolimus, tacrolimus, an analogue thereof, and a combination thereof. The method can include hydrating and/or soaking the coating in the flushing composition at the target site. The method can include inflating the balloon to an inflation diameter such that the coating contacts an interior of the body lumen at the target site. The method can include deflating the balloon. The method can include withdrawing the scope and the balloon catheter from the target site.

In various embodiments of the method, the method is free of damaging, dilating, and/or removing of the stricture or stenosis prior to the insertion of the drug coated balloon catheter. In other embodiments that include damaging, dilating, and/or removing of the stricture of stenosis prior to the insertion of the drug coated balloon catheter, the damaging, dilating, and/or removing of the stricture or stenosis can be performed using any suitable method. The damaging, dilating, and/or removing of the stricture or stenosis can include surgical removal, electrocautery, laser ablation, cryoablation, radiofrequency ablation, mechanical debulking, rigid bronchoscopy dilation, knife-cutting, direct vision internal stricturotomy, use of an uncoated balloon to dilate the stricture or stenosis, or a combination thereof. The damaging, dilating, and/or removing of the stricture or stenosis can include inserting a predilation balloon into the body lumen at the target site, inflating the predilation balloon, and removing the predilation balloon prior to inserting the drug coated balloon catheter. In some embodiments the predilation balloon catheter has cutting or scoring elements on the balloon that are used to break calcified plaque. In some embodiments, the predilation catheter can be shorter and/or of less diameter than the drug-coated balloon treatment catheter. In this scenario, the predilation catheter is positioned such that the center of the balloon body is aligned with the center of the stricture or stenosis. Once inflated, the predilation balloon is deflated and removed and the drug-coated treatment balloon is inserted. The size of the drug coated balloon is chosen such that the balloon diameter and the balloon length is larger than the pre-dilation balloon catheter to ensure the drug coating comes in contact with the entire luminal wall of the predilated stenosis or stricture.

The method includes inserting a balloon catheter through the nasal passage or the mouth and tracking to the recuring airway strictures or stenosis. The inserting the scope and the balloon catheter can include inserting the balloon catheter through a lumen of the scope. The inserting the scope and the balloon catheter can include inserting the balloon catheter and the scope side-by-side. The method can include placing the scope and a proximal edge of the balloon of the balloon catheter at or near the target site. The scope can be any suitable scope for use in the body lumen including the target site, such as an endoscope, rhinolaryngoscope, rhinoscope, bronchoscope, cystoscope, or a combination thereof. The scope can be a rigid scope or a flexible scope. The method can include visualizing positioning of the balloon catheter at the target site with the scope. The method can include visualizing the yielding and dilation of the target site with the scope. The method can include visualizing the inflating with the scope. The method can include the physician/user using the scope to visualize the expansion of the balloon during inflation thereof. The method can include the physician/user using the scope to visualize the expansion of the lumen wall as the inflating balloon presses against the interior of the lumen. The method can include the physician/user using the scope to visualize and ensure complete apposition of the drug coated balloon against the lumen and/or using the scope to visualize and prevent overexpansion of the treated lumen. The method can include the physician/user using the scope to visualize and ensure complete drug coverage of the target site after deflation of the balloon via observation of the drug deposited on the lumen wall.

Various embodiments of the method are free of flushing the target site prior to and/or during the insertion of the balloon catheter to the target site. In other embodiments that include flushing the target site with a flushing composition prior to and/or during the insertion of the balloon catheter to the target site, the method can include flushing the target site prior to inserting a balloon catheter through the nasal passage or the mouth and tracking to the recuring airway stricture or stenosis. The flushing composition can include water, saline, or a combination thereof. In some embodiments, the flushing can be performed before, during, or after the insertion of the balloon catheter to the target site. The hydrating and/or soaking in the flushing composition can be performed for any suitable time period, such as about 0.1 minutes to about 20 minutes, or about 0.1 minutes to about 10 minutes, or about 0.1 minutes to about 5 minutes, or less than or equal to 20 minutes and greater than or equal to 0.1 minutes, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 12, 14, 16, 18, or 19 minutes. In embodiments of the method that are free of flushing of the target site, the balloon catheter can be flushed or soaked prior to insertion (e.g., soaked and/or hydrated outside the body prior to insertion).

In some embodiments, the balloon is inflated until the coating layer contacts walls of the stricture or stenosis and the stricture or stenosis is dilated, with simultaneous transfer of the drug to the stricture or stenosis. In some embodiments, the balloon is inflated until the coating layer contacts walls of the stricture or stenosis, the inflation dilates the stricture or stenosis to increase its diameter, such that the contacting with the stricture or stenosis can provide full circumferential transfer of the drug to the wall of the stricture or stenosis. In some embodiments, the portion of the balloon that includes the drug (e.g., in embodiments including less than 100% of the surface area coated with the drug) can contact the stricture or stenosis uniformly. In other embodiments, the contacting of various portions of the surface of the balloon with the stricture or stenosis is non-uniform.

The inflated diameter of the balloon can be any suitable diameter that is achieved during or throughout the inflation period such that a desired ratio of the inflated balloon diameter to the diameter of the body lumen is achieved. The desired ratio can be in the range of 0.5 to 2.0 or greater than or equal to 0.5 and less than or equal to 0.75, 1.0, 1.1, 1.2, 1.3, 1.4, 1.5, 1.6, 1.7, 1.8, 1.9, or 2.0. The inflated diameter of the balloon can correspond to the pressure used to inflate the balloon during the inflation period. In some embodiments, the inflated pressure can be the nominal pressure for the balloon, and the inflated diameter of the balloon can be about equal to the nominal diameter of the balloon, or can be less than the nominal diameter of the balloon due to constraint from the stricture or stenosis. In some embodiments, the inflated pressure of the balloon during the inflation period can be above or below the nominal pressure and the inflated diameter of the balloon can be, correspondingly, above or below the nominal diameter of the balloon.

The inflating can be performed sufficient to achieve a particular stretch ratio. The stretch ratio is defined herein, unless otherwise indicated, as the ratio of the nominal diameter of the balloon to the diameter of the body lumen in the area being treated by the balloon catheter. The nominal diameter of the balloon is the diameter the balloon achieves in an unrestricted environment at the nominal pressure. The lumen diameter is the average of the diameters of the stricture or stenosis or lesion of the lumen. The inflated balloon diameter can be the actual diameter of the balloon following inflation, which in some embodiments can equal to, less than, or greater than the nominal diameter of the balloon. In various embodiments, the stretch ratio of the balloon catheter of the present invention makes it more effective for treating airways strictures and stenosis than other catheters. During performance of a method of the present invention, the stretch ratio can be selected to be any suitable ratio that achieves the desired ratio of actual inflated balloon diameter to lumen diameter at the range of pressures used during the method. In various embodiments, the stretch ratio of the balloon can be about 1.01 to about 20, 1.31 to 20, or about 1.01 to about 15, or about 1.1 to about 10, 1.2 to 10, 1.3 to 10, 1.31 to 10, 1.4 to 10, 1.5 to 10, 1.6 to 10, 1.7 to 10, 1.8 to 10, 2 to 10, 2.2 to 10, 2.5 to 10, or about 1.0 to about 40 (e.g., less than or equal to 40 and greater than or equal to 1, 1.1, 1.2, 1.4, 1.6, 1.8, 2, 2.5, 3, 4, 5, 6, 7, 8, 9, 10, 12, 14, 16, 18, 20, 22, 24, 26, 28, 30, 32, 34, 36, or 38); such a stretch ratio can result in a desired ratio of inflated balloon diameter to lumen diameter at the pressures used during the inflation period that can be the same, similar to, or different than the stretch ratio, such as about 1.01 to about 20, 1.31 to 40, or about 1.01 to about 15, or about 1.1 to about 10, 1.2 to 10, 1.3 to 10, 1.31 to 10, 1.4 to 10, 1.5 to 10, 1.6 to 10, 1.7 to 10, 1.8 to 10, 2 to 10, 2.2 to 10, 2.5 to 10, or about 1.0 to about 40 (e.g., less than or equal to 40 and greater than or equal to 1, 1.1, 1.2, 1.4, 1.6, 1.8, 2, 2.5, 3, 4, 5, 6, 7, 8, 9, 10, 12, 14, 16, 18, 20, 22, 24, 26, 28, 30, 32, 34, 36, or 38).

The inflating can be performed at least until the target site yields and is dilated. The inflating can be performed such that the ratio of the inflation diameter to a normative body lumen diameter at the target site is about 1.0 to about 20, such as less than or equal to 20 and greater than or equal to 1, 1.1, 1.2, 1.4, 1.6, 1.8, 2, 2.5, 3, 4, 5, 6, 7, 8, 9, 10, 11, 12, 13, 14, 15, 16, 17, 18, or 19. The inflating can be performed such that the ratio of the inflation diameter to a normative body lumen diameter at the target site is about 1.0, 1.1, 1.2, or 1.31 to 10. The inflating can be performed such that the balloon is inflated to a pressure that is equal to or greater than a nominal pressure of the balloon. The inflating can be performed such that a stretch ratio of the inflated diameter of the balloon to a normative body lumen diameter at the target site is about 1.0 to about 20. The inflating can be performed such that a stretch ratio of the inflated diameter of the balloon to a normative body lumen diameter at the target site is about 1.0, 1.1, 1.2, or 1.31 to 10, or about 1.0 to about 20, such as less than or equal to 20 and greater than or equal to 1, 1.1, 1.2, 1.4, 1.6, 1.8, 2, 2.5, 3, 4, 5, 6, 7, 8, 9, 10, 11, 12, 13, 14, 15, 16, 17, 18, or 19. The inflating can be performed such that a ratio of the inflation diameter to a normative body lumen diameter at the target site is about 1.0 to 20, and such that a stretch ratio of the inflated diameter of the balloon to a normative body lumen diameter at the target site of about 1.0 to about 20. The inflating can be performed such that the balloon is inflated to a pressure greater than a nominal pressure of the balloon, and a nominal inflated diameter of the balloon is less than the inflated diameter. Feature (a), or (b), or (c), or (a) and (b), or (a) and (c), or (b) and (c), or (a) and (b) and (c), can be present: (a) the ratio of the inflated balloon diameter to a body lumen diameter at the target site is about 1.0 to about 40 (e.g., less than or equal to 40 and greater than or equal to 1, 1.1, 1.2, 1.4, 1.6, 1.8, 2, 2.5, 3, 4, 5, 6, 7, 8, 9, 10, 12, 14, 16, 18, 20, 22, 24, 26, 28, 30, 32, 34, 36, or 38); or (b) the inflating includes inflating the balloon to a pressure equal to or greater than a nominal pressure of the balloon catheter, and the stretch ratio of a nominal diameter of the balloon catheter to a body lumen diameter at the target site is about 1.0 to about 40 (e.g., less than or equal to 40 and greater than or equal to 1, 1.1, 1.2, 1.4, 1.6, 1.8, 2, 2.5, 3, 4, 5, 6, 7, 8, 9, 10, 12, 14, 16, 18, 20, 22, 24, 26, 28, 30, 32, 34, 36, or 38); or (c) the inflating includes inflating to a pressure greater than the nominal pressure of the balloon catheter, and the nominal diameter of the balloon catheter is less than the inflated balloon diameter; or (d) a combination of (a), (b), and (c). The inflating can include observing pressure within the balloon (e.g., via a pressure gauge external to the patient). The inflating can include inflating the balloon to a first pressure, allowing pressure within the balloon to stabilize while maintaining the first pressure in the balloon for a stabilization period, then resuming increasing pressure in the balloon until the inflation diameter is achieved.

The method can include maintaining the inflation diameter for a suitable period of time. Maintaining the inflation diameter can include keeping the inflation diameter at or above a particular desired diameter. The inflation diameter can increase under a consistent inflation pressure as the stricture or stenosis yields. The method can include maintaining the inflation diameter by keeping the balloon inflated for 1 minute to 7 days, 1 minute to 1 day, 1 minute to 10 minutes, or less than or equal to 7 days and greater than or equal to 1 minute, 2 minutes, 3, 4, 5, 6, 7, 8, 9, 10, 12, 14, 16, 18, 20, 25, 30, 35, 40, 45, 50, 55 minutes, 1 hour, 2, 4, 6, 8, 10, 12, 14, 16, 18, 20, 22 hours, 1 day, 2 days, 3, 4, 5, or 6 days. The method can include maintaining the inflation diameter for a duration sufficient to release the drug into tissue of the target site and/or to prevent or reduce bleeding. Balloon Catheter.

The balloon catheter can include an elongated balloon. The balloon catheter can also include a coating layer overlying an exterior surface of the balloon. The coating layer can include one or more additives and an initial drug load of a therapeutic agent chosen from paclitaxel, docetaxel, taxol, rapamycin, sirolimus, zotarolimus, everolimus, tacrolimus, an analogue thereof, and a combination thereof.

The balloon catheter can include a fixed wire balloon catheter, over the wire balloon catheter, rapid exchange balloon catheter, a perfusion balloon catheter, a spaced double balloon, a cutting balloon catheter, a scoring balloon catheter, or an infusion catheter (e.g., a distal perforated drug infusion tube, a perforated balloon, spaced double balloon, porous balloon, or a weeping balloon).

The elongated balloon can have a length of about 20 mm to about 300 mm, or about 20 mm to about 160 mm, or less than or equal to about 300 mm and greater than or equal to about 20 mm, 25, 30, 35, 40, 45, 50, 55, 60, 65, 70, 75, 80, 85, 90, 95, 100, 105, 110, 115, 120, 125, 130, 135, 140, 145, 150, 175, 200, 225, 250, 275, or 290 mm.

The balloon can include a main diameter that is a nominal inflated diameter (e.g., a nominal diameter) of at least 1 mm, or at least 5 mm, or at least 10 mm, or at least 13 mm, or at least 15 mm, or at least 20 mm, or at least 30 mm, or at least 35 mm, or 1-50 mm, 1-40 mm, or 1-30 mm, or less than or equal to 50 mm and greater than or equal to 1 mm, 2, 3, 4, 5, 6, 8, 10, 12, 14, 16, 18, 20, 22, 24, 26, 28, 30, 32, 34, 36, 38, 40, 42, 44, 46, or 48 mm. For a balloon including a neck, the main diameter is the diameter of the larger sections of the balloon. The nominal diameter is determined at the nominal inflation pressure of the balloon, is the diameter normally obtained at the nominal pressure in an unrestricted environment.

In some embodiments, the inflated pressure used to determine the main diameter can be any pressure that eliminates any folded or creased areas of the balloon and achieves taughtness of the balloon. The inflated pressure used to determine the main diameter can be a pressure such that the inflated balloon has a shape and size that corresponds to the desired shape and size of the balloon during the intended treatment of the body lumen. The inflated pressure used to determine the main diameter can be the nominal pressure of the balloon, such that the nominal diameter of the balloon catheter is equal to the main diameter of the balloon. In some embodiments, the inflated diameter of the balloon at the target site during inflation to the nominal pressure is equal to the nominal diameter; however, during actual use, some strictures can prevent achievement of the nominal diameter, or can constrain the inflated balloon to form "dog-bone" shape. The nominal balloon diameter at predetermined pressure (e.g., 2 atm, 3 atm, 6 atm, or 9 atm) can be different for different diameters of balloons for various diseases. For example, nominal diameters of sinus stricture or stenosis balloons can be 6 mm, 8 mm, 10 mm, 12 mm, and 14 mm with balloon lengths of 20 mm, 25 mm, and 30 mm for 6 mm, 8 mm, 10 mm, 12 mm, and 14 mm balloon catheters at 4 atm, 5 atm, 6 atm, 8 atm, or 12 atm inflation. The nominal diameters of the airway stricture or stenosis balloons can be 25 mm, and 30 mm with balloon lengths of 20 mm, 25 mm, 30 mm, 35 mm, 40 mm, 45 mm, 50 mm, 55 mm, and 60 mm balloon catheters at nominal pressure of 2 atm, 3 atm, 4 atm, 6 atm, or 9 atm inflation. Nominal pressure is the pressure required to bring the balloon to its labeled nominal diameter in an unconstrained pressure ramp test. Nominal diameter is the desired diameter that the product is labeled with. All physicians purchase balloons and select balloons for use according to the nominal diameter. The rated burst pressure is the maximum pressure that the balloon can be inflated to and have a very high confidence that it will not burst, a labeling requirement for balloon catheters that is calculated from a statistical analysis of the pressures observed when the balloons burst in an unconstrained pressure ramp test.

Examples of properties of balloon catheter for treating recurring airway strictures or stenosis are shown in Table 1.

TABLE 1

Examples of properties of balloon catheters
for treating the recurring airway strictures.

| Nominal diameter (mm) | Rated burst pressure diameter (mm) | Nominal pressure (atm) | Rated burst pressure (atm) | Compliance (%) |
|---|---|---|---|---|
| 4 | 6 | 3 | 12 | 50 |
| 6 | 8 | 3 | 10 | 30 |
| 8 | 10 | 3 | 9 | 25 |
| 10 | 12 | 3 | 8 | 20 |
| 12 | 15 | 3 | 8 | 17 |
| 15 | 18 | 3 | 7 | 20 |
| 18 | 20 | 3 | 6 | 11 |
| 20 | 23 | 3 | 6 | 15 |
| 23 | 25 | 3 | 6 | 9 |
| 30 | 34 | 2 | 4 | 13 |

TABLE 1-continued

Examples of properties of balloon catheters
for treating the recurring airway strictures.

| Nominal diameter (mm) | Rated burst pressure diameter (mm) | Nominal pressure (atm) | Rated burst pressure (atm) | Compliance (%) |
|---|---|---|---|---|
| 35 | 40 | 2 | 4 | 14 |
| 40 | 45 | 2 | 4 | 12 |

In some embodiments, the balloon catheter properties are equal or similar to those given in Table 2, a single balloon catheter having the ability to achieve a wide range of balloon diameters at relatively high working pressures compared to conventional compliant balloons. Balloons in Table 2 have a unique feature that there are three increasing balloon diameters at three increasing inflation pressure stages. The nominal inflation diameter is the diameter at stage I. The diameter increases about 0.5-4 mm, preferably 0.75-3 mm, most preferably 0.9-2 mm for every stage of pressure increase. For example, a balloon that has a diameter of 15 mm at Pressure I (3 atm) has a diameter of 16.5 mm at pressure II (4.5 atm) and has a diameter of 18 mm at pressure III (7 atm).

TABLE 2

Examples of properties of balloon catheters
for treating airway strictures and stenosis.

| Three inflation pressure stages (atm) | Diameter at pressure stage I (mm) (Nominal Diameter) | Diameter at pressure stage II (mm) | Diameter at pressure stage III (mm) |
|---|---|---|---|
| 3, 6, 10 | 4 | 5 | 6 |
| 3, 6, 10 | 6 | 7 | 8 |
| 3, 5.5, 9 | 8 | 9 | 10 |
| 3, 5, 8 | 10 | 11 | 12 |
| 3, 4.5, 8 | 12 | 13.5 | 15 |
| 3, 4.5, 7 | 15 | 16.5 | 18 |
| 3, 4.5, 6 | 18 | 19 | 20 |
| 3, 4.5, 5.5 | 20 | 21.5 | 23 |
| 3, 4, 5 | 23 | 24 | 25 |
| 2, 3.5, 4.5 | 30 | 32.5 | 35 |
| 2, 3, 4 | 35 | 37.5 | 40 |
| 2, 3, 4 | 40 | 42.5 | 45 |

In various embodiments, the balloon catheter can be sufficient such that at a predetermined pressure (e.g., the nominal pressure) the balloon can have any suitable ratio of inflated balloon catheter diameter to a diameter of the body lumen at the location of treatment; for example, at a pressure of about 1 atm (~101 kPa) to about 30 atm (~3040 kPa) (e.g., about 1 atm or less, or less than, equal to, or more than about 4 atm, 5, 6, 7, 8, 9, 10, 11, 12, 13, 14, 15, 16, 17, 18, 19, 20, 22, 24, 26, 28, or about 30 atm or more).

The balloon catheter can include the elongated balloon and can be free of other balloons. In other embodiments, the balloon catheter can include more than one balloon.

The balloon can be substantially free of neck sections between a proximal and a distal end of the balloon. In other embodiments, the balloon can include at least one neck section on the balloon including a smaller diameter than a main diameter of the balloon when the balloon is inflated, the at least one neck section dividing the balloon into at least two main sections each having a diameter. The neck section can include a central narrow portion having the smallest diameter of the neck section, and an adjacent portion that can have a varying diameter and that occurs between the central narrow portion and portions of the balloons having the main diameter. During inflation, the neck section in combination with the at least two main sections can together anchor the balloon at the target site in the body lumen and help to avoid slippage and thereby help to avoid damaging healthy or unintended body lumen. In various embodiments, the one or more neck sections can allow the balloon catheter to stay in place during treatment more consistently and effectively to dilate the stricture or stenosis and deliver the drug as compared to other balloon catheters lacking such a neck section or configuration of neck sections. When the diameter of a neck section is referred to herein, it refers to the diameter of the central narrow portion which has the smallest diameter, and not to the tapered sections, unless otherwise indicated. The tapered sections of the balloon can be rigid, flexible (e.g., elastic), or a combination thereof. The diameter of the at least two main sections can be equal to the main diameter of the elongated balloon, or the at least one neck section has a diameter that is about 5% to about 99% of the diameter of at least one of the at least two main sections. The at least one neck section can have a diameter that is independently about 5 mm to about 35 mm, or 1 mm to 40 mm, or less than or equal to 40 mm and greater than or equal to 1 mm, 2, 3, 4, 5, 6, 8, 10, 12, 14, 16, 18, 20, 22, 24, 26, 28, 30, 32, 34, 36, or 38 mm. The one neck section can have any suitable position on the balloon, such as approximately centered with respect to the balloon length, or off-center with respect to the balloon length. The one neck section can be off-center with respect to the length of the balloon and can be at a distal end of the balloon. An embodiment of the balloon including one neck section that is off-center with respect to the length of the balloon is illustrated in FIG. 1A.

The diameter of the at least one neck section can be substantially static during inflation of the balloon, such that the diameter of the neck section remains substantially static during inflation of the balloon. The neck section can be a rigid or semi-rigid neck section. The at least one neck section can include a substantially nonelastic (e.g., non-compliant, or minimally compliant) portion of the balloon, a reinforced portion of the balloon, or a combination thereof. The at least one neck section can include an inelastic material around a circumference of the neck section. The inelastic material can include a suture or monofilament or multifilaments of such material, such as nylon, polyamide, an aromatic polyamide, ultra high molecular weight polyethylene (UHMWPE), a polyester, an aromatic polyester, polyethylene terephthalate (PET) or a combination thereof.

The diameter of the at least two main sections can be about 1 mm to about 50 mm, about 1 mm to about 35 mm, about 1 mm to about 30 mm, about 1 mm to about 20 mm, or about 5 mm to about 45 mm, or less than or equal to 50 mm and greater than or equal to 1 mm, 2, 3, 4, 5, 6, 8, 10, 12, 14, 16, 18, 20, 22, 24, 26, 28, 30, 32, 34, 36, 38, 40, 42, 44, 46, or 48 mm.

The at least one neck section can be about 1% to about 50% of the balloon length, or less or equal to about 50% and greater than or equal to 1%, 2, 3, 4, 5, 6, 7, 8, 9, 10, 12, 14, 16, 18, 20, 22, 24, 26, 28, 30, 32, 34, 36, 38, 40, 42, 44, 46, or 48%.

The at least one neck section can be one neck section and the balloon can be free of other neck sections, such that the balloon includes two main sections separated by one neck section. The at least one neck section can be two neck sections and the balloon can be free of other neck sections.

Figure 1B:
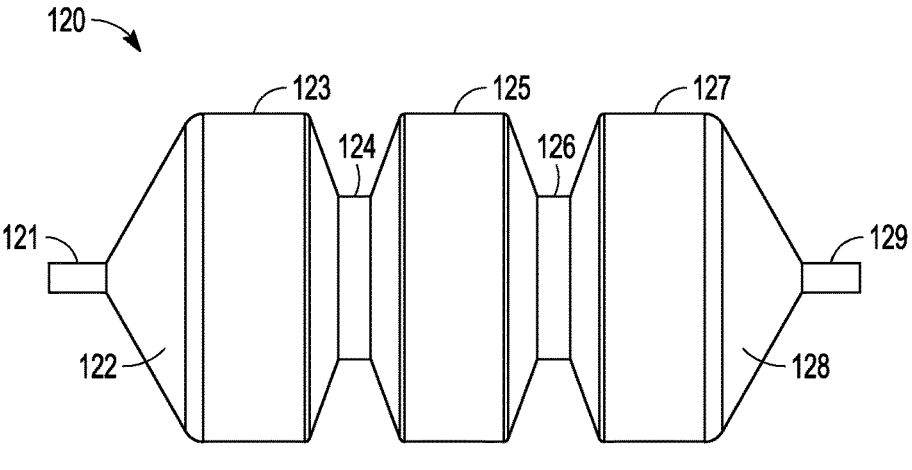
FIG. 1B illustrates a balloon catheter having two neck sections, in accordance with various embodiments.

The two neck sections can have about the same diameter. One of the two neck sections can have a smaller diameter than the other neck section. The two neck sections can be symmetrically or asymmetrically located with respect to the center of the balloon length. The three main sections can have approximately equal length or can have different lengths. FIG. 1B illustrates an embodiment of a balloon catheter having two neck sections with three main sections, wherein the neck sections are symmetrically located about the center of the length of the balloon, and wherein the three main sections of the balloon have about the same length.

Figure 1C:
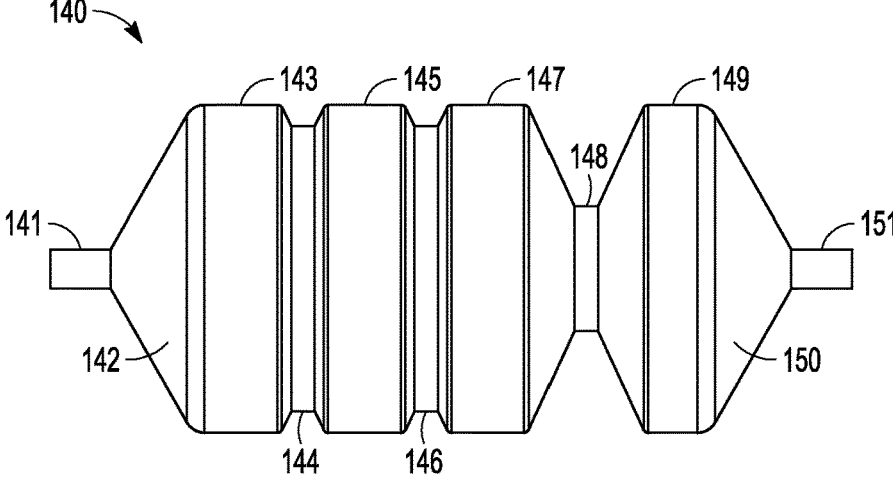
FIG. 1C illustrates a balloon catheter having three neck sections, in accordance with various embodiments.

The balloon catheter can include three of the main sections separated by the two neck sections. The at least one neck section can be three neck sections, wherein the balloon is free of other neck sections. The three neck sections can be arranged to provide four of the main sections separated by the three neck sections. The three neck sections can be positioned in any suitable way along the length of the balloon. The four main sections formed by the three neck sections can have equal or different lengths. The three neck sections can have equal diameters, or different diameters. In some embodiments two of the neck sections have an equal diameter that is smaller than the diameter of the other neck section. FIG. 1C illustrates an embodiment of a balloon catheter having three neck sections with four main sections each having an approximately equal length, wherein two of the neck sections have an equal diameter that is smaller than the diameter of the other neck section.

In some embodiments, the balloon neck section can be semi-compliant and expand at different rates than the main balloon body. The neck section compliance can be more, less or equal to the compliance of the balloon body. Table 3 illustrates example measurements of a balloon that has neck section that expands more than the balloon body. The expansion rate of the neck diameter can be higher than the expansion rate of the diameter of the main body section in the tested pressure range of 1-5 atm. The expansion rate of the neck diameter can be in the range of 1.1 to 10 times that of the diameter of the main body section (main diameter) in the tested pressure range of 1-5 atm, such as in the range of 2 to 6 times the main diameter. The expansion rate of the neck diameter can be 12.38% per atm. The expansion rate of the body diameter can be 2.4% per atm. The difference of the expansion rates can be 9.98% per atm. Table 4 illustrates example measurements of a balloon that has a neck section that expands less than the balloon body when inflated from 2 atmospheres to 4 atmospheres. The expansion rate of the neck diameter can be less than the expansion rate of the diameter of the main body section in the tested pressure range of 2-4 atm.

TABLE 3

| Example measurements of a balloon that has neck section that expands more than the balloon body. | | | | |
|---|---|---|---|---|
| Balloon Pressure [atm] | Neck Diameter [mm] | Body Diameter [mm] | Body Compliance | Neck Compliance |
| 1 | 21.5 | 39.0 | 2.3% (1-2 atm) | 12.2% (1-2 atm) |
| 2 | 24.0 | 40.0 | 2.4% (2-3 atm) | 15.7% (2-3 atm) |
| 3 | 27.5 | 40.5 | 2.6% (3-4 atm) | 13.4% (3-4 atm) |
| 4 | 31.5 | 41.5 | 2.3% (4-5 atm) | 8.2% (4-5 atm) |
| 5 | 34.0 | 42.5 | — | — |

TABLE 4

| Example measurements of a balloon that has a neck section that expands less than the balloon body. | | | | |
|---|---|---|---|---|
| Balloon Pressure [atm] | Neck Diameter [mm] | Body Diameter [mm] | Body Compliance | Neck Compliance |
| 2 | 15.28 | 34.06 | 8.7% (2-4 atm) | 0.4% (2-4 atm) |
| 4 | 15.34 | 37.02 | — | — |

The neck section can create a wedge of tissue between the larger diameter sections of the balloon that can hold the balloon in place. The larger sections of the balloon cannot overcome the tissue barriers created at the neck section, thus the balloon with the neck section can prevent, reduce, or minimize balloon migration during inflation. Neck section placement can be designed to facilitate the greatest increase in traction while still maintaining treatment efficacy.

The balloon catheter can include a catheter shaft on a longitudinal end of the balloon, the catheter shaft including an interior lumen for delivery of a gas, liquid, or a combination thereof, to the balloon interior. The balloon catheter can include an atraumatic Coude tip.

The balloon catheter can be a fixed wire balloon catheter. The balloon catheter can be an over-the-wire balloon catheter. The balloon catheter can be a rapid exchange balloon catheter. The outer shaft can be bonded to the proximal balloon neck (e.g., on the proximal end of the balloon, inserted into the body after insertion of the distal end), with the distal end of the tapered wire bonded with a distal neck of balloon, and with the proximal ends of the wire and outer shaft bonded with the hub (e.g., a valve, connector, or adapter) at the proximal end of the balloon catheter. The balloon catheter can be a moveable wire catheter. The outer shaft is bonded to the proximal balloon neck, the distal end of the tapered wire is bonded with the distal neck of balloon, the proximal end of the wire is free to move relative to the hub at the proximal end of the balloon catheter. The balloon catheter can be an over-the wire balloon catheter. The balloon catheter can be a rapid exchanged balloon catheter. The balloon catheter can include a catheter shaft on a longitudinal end of the balloon (e.g., on the proximal end of the balloon, inserted into the body after insertion of the distal end), the catheter shaft including an interior lumen for delivery of air, liquid, or a combination thereof, to the balloon interior. The catheter shaft can include a thermoplastic material that is thermally attached (e.g., attached via heating or melting) to the balloon, such as a high durometer material, such as a material similar or identical to the balloon material, such as polyamides, nylon (e.g., nylon 6,6, or nylon 12), polyether block amide (PEBA), 70 D polyether block amide (PEBA), 72 D polyether block amide (PEBA), 74 D polyether block amide (PEBA), polyethylene tereph-thalate (PET), polyvinylchloride (PVC), polyester, polyurethane, derivatives thereof, or a combination thereof. In some embodiments, the catheter shaft can be a scope (e.g., cystoscope). A high durometer material can help to prevent, reduce, or minimize crushing, and can allow pushability and flexibility. The catheter shaft outer diameter can be sized to allow passage through the working channel of a scope. A fluidic connection between the inner lumen and the inside of the balloon can be included, such as holes in the catheter shaft underneath the balloon attachment point to allow inflation of the balloon by instilling media through the inner lumen.

The catheter shaft at an end that remains outside the body (e.g., proximal end) can include a hub (e.g., a valve, connector, or adapter) that provides a connection to the interior lumen of the catheter shaft. During inflation, the hub (e.g., when closed, or always), can prevent backflow of fluid or air from the balloon. The hub can be can include any suitable valve, such as a Tuohy Borst adapter. The Tuohy Borst adapter is a compression sealing device that can be placed over the catheter shaft and tightened to provide a liquid/air tight connection to the inner lumen of the catheter shaft. A one-way stopcock can allow control over fluid flow into the balloon and can connects via a standard Luer to an inflation device.

The proximal side of the catheter shaft can include a hub or any other attachment manifold to connect and infuse a liquid, air, or other gas through the catheter to inflate the balloon, allow passage of a guidewire, allow urine to drain, or to make any other suitable connection to the catheter shaft. The connections to the hub or attachment manifold can be made via any suitable one or more connections, such as a single female or male Luer hub, or a Luer manifold with multiple channels. The hub or manifold can be constructed with any appropriate biocompatible material such as polycarbonate, acrylonitrile butadiene styrene, nylon, PEBAX®, silicone, any other polymeric material capable of being molded, or a combination thereof. The hub can be attached to the catheter in any suitable way, such as using adhesive (e.g., cyanoacrylate adhesive, silicone adhesive, epoxy, any other adhesive suitable for the substrates, or a combination thereof) or using chemical bonding. The hub or manifold can be over-molded to the catheter shaft to directly fuse it to the catheter shaft. The catheter shaft can include a strain-relief component at the junction between the catheter shaft and the hub or manifold. The strain-relief component can help to prevent kinking. The strain-relief component can include a polyolefin, PET, FEP, another heat-shrinkable material, or a combination thereof. The strain-relief component can be a heat shrink. The strain-relief component can be a flexible molded material that interfaces with the hub (e.g., the strain-relief component can be attached to the hub).

The balloon catheter can include a catheter tip at a longitudinal end of the balloon, at the distal end which is inserted into the body first. The catheter tip can facilitate passage of the balloon through the body lumen. The tip can be an atraumatic tip that helps prevent damage to the body lumen during insertion therein. The tip can be a Coude atraumatic tip. The atraumatic Coude tip is designed to facilitate passage of the catheter through the bends in body lumen while preventing damage to the walls of the body lumen during tracking. The tip can be a low durometer biocompatible material overmolded onto the catheter shaft or adhesively bonded onto the shaft. For example, the Coude tip can be formed from a PEBAX® or liquid silicone rubber.

Figure 2:
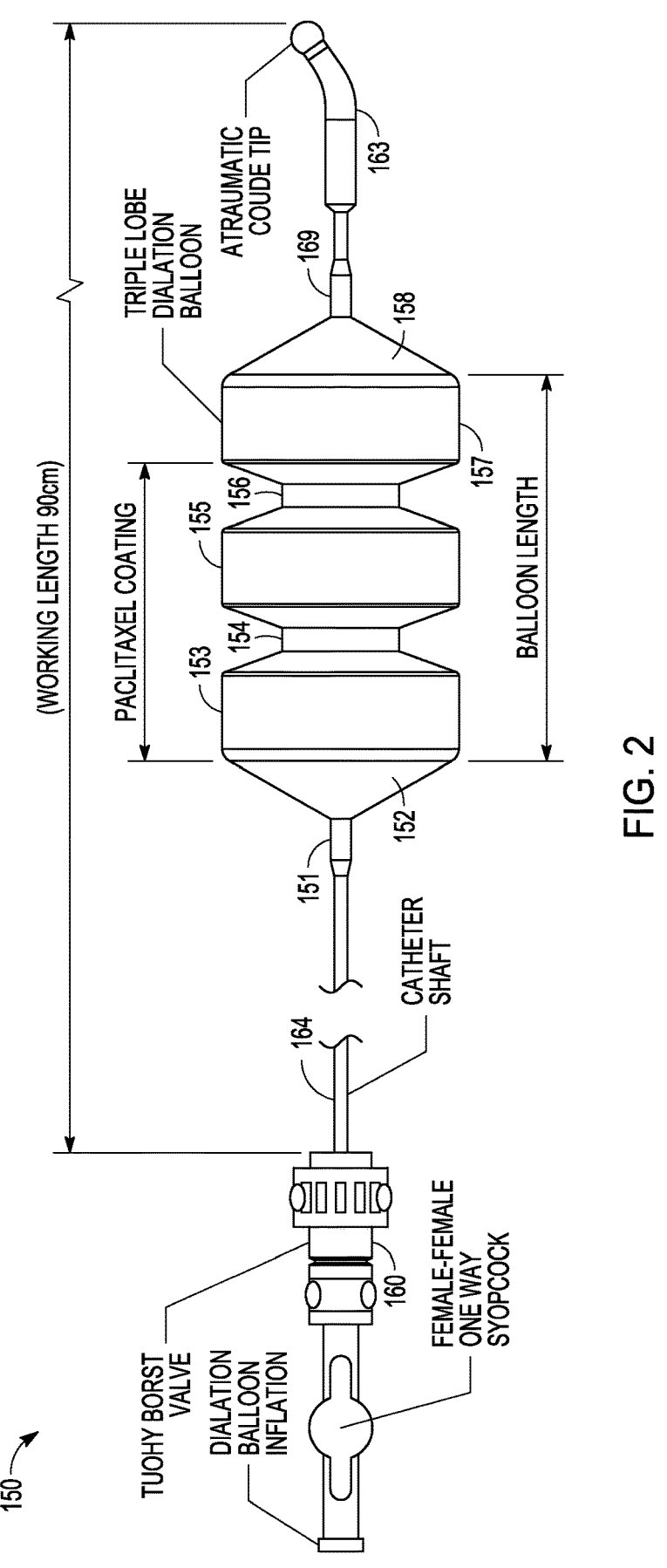
FIG. 2 illustrates a two-necked drug-coated balloon catheter including a catheter shaft, catheter tip, and Tuohy Borst adapter, in accordance with various embodiments (the balloon catheter includes a fixed wire, over the wire, and rapid exchanged balloon catheters details not shown in FIG. 2), in accordance with various embodiments.

FIG. 2 illustrates an embodiment of the balloon catheter including a catheter shaft, catheter tip, and Tuohy Borst adapter/stopcock assembly. All materials can be biocompatible. The balloon is coated with a paclitaxel solution but may be coated with any multitude of other drugs or biologics that could facilitate improvement of BPH symptoms. In FIG. 2, only the proximal two main sections of the balloon are coated with drug.

The balloon catheter can include an inflation device including a pressure gauge or pressure sensor, the inflation device fluidly connected to a catheter shaft connected to the balloon catheter. The gauge or sensor can be used to monitor and/or observe the pressure of the balloon during inflation thereof.

The balloons shown in FIGS. 1A, 1B, 1C, and 2 can be blow molded in a mold that includes the main sections and the neck sections. A tube of balloon material can be inserted into a mold with the desired shape. The balloon material tube may be prestretched. The balloon mold has a shape that corresponds to the balloons shown in FIG. 1A, 1B, 1C, or 2. For a balloon catheter including one neck, this will include a proximal cone, at least one main body section, at least one neck section, at least one more main body section, and the distal cone. The balloon material can be any of polyesters, polyamides, nylon 12, nylon 11, polyamide 12, block copolymers of polyether and polyamide, PEBAX®, polyurethanes, and block copolymers of polyether and polyester. The tube and mold are heated to a temperature above the glass transition temperature of the tube of balloon material and pressurized with gas, air, fluid, or the like resulting in the material of the tube taking the shape of the mold. The formed balloon can then be cooled, trimmed, and is then ready to be attached to the catheter. The balloon catheter shaft can be constructed of polyether-amide block copolymers, polyamides, nylons, polyesters, polyethylene terephthalate, or any other semi-compliant to non-compliant polymer including their blends. The balloon catheter shaft can be constructed using a rigid material such as stainless steel, polycarbonate, titanium, PEEK (polyether ether ketone), or any other rigid biocompatible material. The balloon catheter shaft can include as polyamides, nylon (e.g., nylon 6,6, or nylon 12), a polyether block amide (PEBA) (e.g., 35D PEBA, 55D PEBA, 72D PEBA, or 74D PEBA), polyurethanes, silicones, rubbers, another thermoplastic polymer, or a combination thereof. The catheter shaft can be uniform in composition or can include a combination of materials that are distributed along one or more portions of the catheter shaft. The catheter shaft can be an extruded catheter shaft. In some embodiments, the catheter shaft can include an elongated rigid component, such as a rod, mandrel, or wire, aligned longitudinally with the catheter shaft.

After the balloon is attached to a catheter, the balloon can be inflated at a low pressure and a neck section reinforcement can be attached to the neck region. The neck section reinforcement is used to control the expansion of the neck section during balloon expansion. The neck section may be a substantially nonelastic portion of the balloon, a reinforced portion of the balloon, or a combination thereof. The neck section can include an inelastic material circulated around a circumference of the neck section, such as a suture or monofilament or multifilaments of such material, such as steel, stainless steel, nitinol, tungsten, aluminum, copper, silver, gold, platinum, iridium, superalloys contain elements, including nickel (Ni) chromium (Cr), aluminum (Al), titanium (Ti), molybdenum (Mo), tungsten (W), niobium (Nb), tantalum (Ta) and cobalt (Co), nylon, polyamide, aromatic polyamides, ultra high molecular weight polyethylene (UHMWPE), polyesters, aromatic polyesters, polyethylene terephthalate (PET) or a combination thereof. In some embodiments, the polymer material is in strand or filament form and is wrapped numerous times around the neck section and then held in place by using two or more spots of glue or adhesive.

The main sections of the balloon may be formed with identical or similar diameters. In some embodiments, the diameters of the various main sections may differ from each other by as much as 30%, when measured at nominal balloon diameter. In FIGS. 1A, 1B, 1C, and 2, the main sections of the balloon are shown with equal diameters, that is the diameter of each main section is constant. In practice, at higher pressures, the diameter of the main sections can become slightly bowed out, in that the diameter of the mid part of the main sections may have a slightly larger diameter than the edges of the main sections near the balloon cone and/or near the neck sections.

Figure 3:
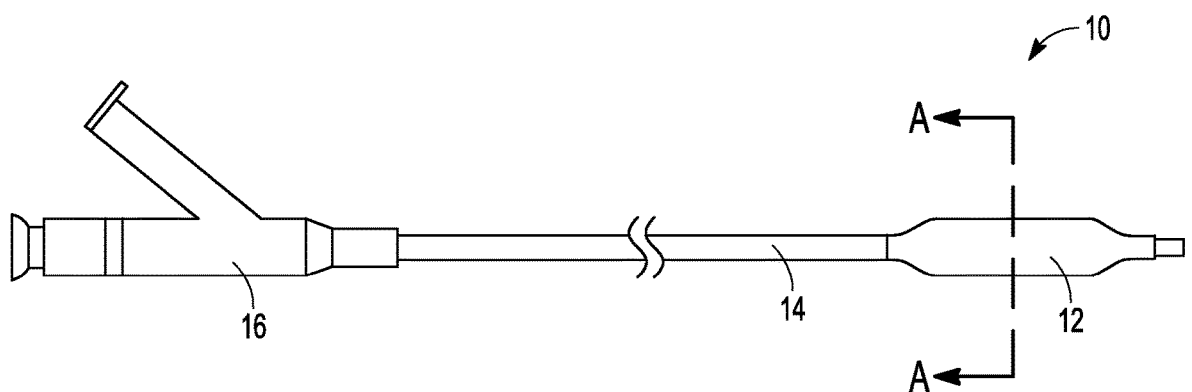
FIG. 3 is a perspective view of an embodiment of a balloon catheter according to the present invention (the balloon catheter includes a fixed wire, over the wire, and rapid exchanged balloon catheters details not shown in FIG. 3), in accordance with various embodiments.

For embodiments where the balloon has neck and main sections, as shown in FIGS. 1A, 1B, 1C, and 2, and where the balloon does not have any neck sections, as shown in FIG. 3, after the balloon catheter is assembled, the balloon may be coated with the at least one water-soluble additive and drug as discussed herein. In some embodiments where the balloon has multiple main sections, the distal main section may not be coated. The balloon may be coated according to the process discussed herein. If a sheath is used, it may be put over the balloon after the balloon is coated. The catheter can then be packaged, sterilized, and labeled as is known in the art.

The balloon catheter can be any suitable catheter for the desired use, including conventional balloon catheters known to one of ordinary skill in the art. For example, as shown in FIG. 3, balloon catheter 10 can include an expandable, inflatable balloon 12 at a distal end of the catheter 10, a handle assembly 16 at a proximal end of the catheter 10, and an elongate flexible member 14 extending between the proximal and distal ends. Handle assembly 16 can connect to and/or receive one or more suitable medical devices, such as a source of inflation media (e.g., air, saline, or contrast media). Flexible member 14 can be a tube made of suitable biocompatible material and having one or more lumens therein. At least one of the lumens is configured to receive inflation media and pass such media to balloon 12 for its expansion. The balloon catheter can be a rapid exchange or over-the-wire catheter and made of any suitable biocompatible material. The material of balloon 12 can include one or more of polyesters, polyamides, nylon 12, nylon 11, polyamide 12, block copolymers of polyether and polyamide, PEBAX®, polyurethanes, and block copolymers of polyether and polyester.

After the deflation and withdrawal from the target site the balloon catheter can include a residual drug amount that is less than 100 wt % of the initial drug load. After the deflation and withdrawal from the target site the balloon catheter can include a residual drug amount that is about 70 wt % or less of the initial drug load, or that is about 0 wt % to about 99 wt % of the initial drug load, or 1 wt % to 90 wt %, 5 wt % to 90 wt %, 10 wt % to 90 wt %, or less than or equal to 99 wt % and greater than or equal to 0 wt %, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 72, 74, 76, 78, 80, 81, 82, 83, 84, 85, 86, 87, 88, 89, 90, 91, 92, 93, 94, 95, 96, 97, or 98 wt %.

The initial drug load can be from about 1 microgram to about 20 micrograms of the therapeutic agent per square millimeter of the balloon, measured when the balloon is at its nominal inflated diameter, or about 2 to about 6 micrograms of the therapeutic agent per square millimeter of the balloon, or less than or equal to about 20 micrograms per $mm^2$ and greater than or equal to about 1 microgram per $mm^2$, 2, 3, 4, 5, 6, 7, 8, 9, 10, 11, 12, 13, 14, 15, 16, 17, 18, 19 micrograms per $mm^2$.

A ratio by weight of the therapeutic agent in the coating layer to the total weight of the one or more additives in the coating layer can be from about 0.05 to about 20, about 0.5 to about 8, about 2 to about 6, or less than or equal to about 20 and greater than or equal to about 0.05, 0.1, 0.2, 0.3, 0.4, 0.5, 0.6, 0.7, 0.8, 0.9, 1, 1.2, 1.4, 1.6, 1.8, 2, 2.5, 3, 3.5, 4, 4.5, 5, 6, 7, 8, 9, 10, 11, 12, 13, 14, 15, 16, 17, 18, or 19. The drug coating can cover any suitable proportion of the exterior surface of the balloon (e.g., proportion of the surface of the balloon that obtains the main diameter during inflation to the nominal pressure, excluding necks and end-cones), such as about 1% to about 100%, or about 50% to about 100%, to about 80% to about 100%, or about 100% or less, or less than, equal to, or greater than 20%, 30, 40, 50, 60, 70, 75, 80, 85, 90, 95, 96, 97, 98, 99, or about 100% or more.

The balloon catheter can further include a sheath covering the elongated balloon. The method can include removing the sheath before the inflating.

The catheter shaft, the balloon, or a combination thereof, can include single or multiple markings along its length to aid in positioning and alignment with certain anatomical structures. The markings can have any suitable orientation, such as circumferential, or longitudinally along the catheter shaft or balloon. Marks on the catheter shaft or balloon can be used to aid in positioning the balloon at the target site, indicate that the balloon is fully recovered in the sheath, or locate the device within a patient's anatomy. Markings on the catheter shaft can be visualized using a scope, or with the unaided eye, or markings can include radiologically distinguishable components such as radiopaque materials. Markings can be created by thermally bonding polymer to the surface of the catheter shaft having a distinguishable color, via pad print, via laser marking, or via any other method.

Figure 4C:
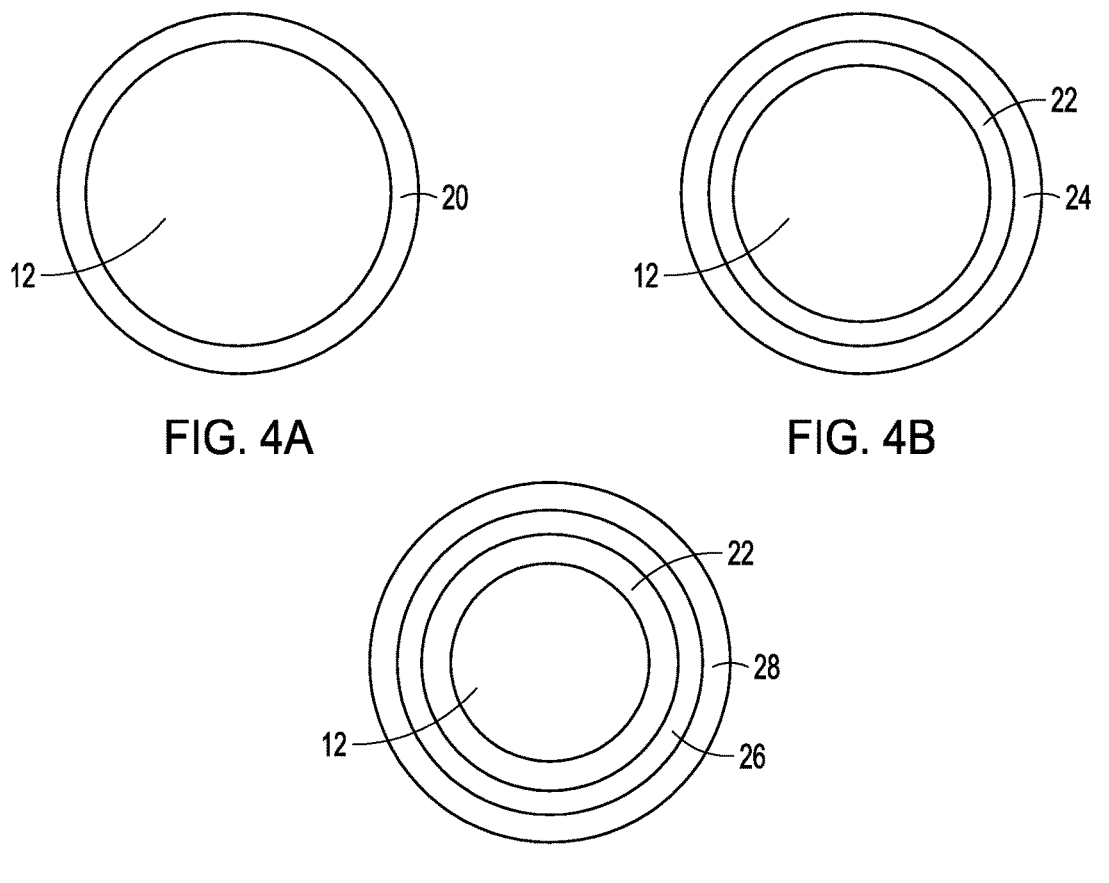

FIGS. 4A-4C are cross-sectional views of different embodiments of the distal portion of the balloon catheter of FIG. 3, taken along line A-A, showing exemplary coating layers. In some embodiments, the balloon can optionally include an adherent layer. For example, as shown in the embodiment depicted in FIG. 4A, the balloon 12 is coated with a layer 20 that includes a therapeutic agent and an additive. In some embodiments, the layer consists essentially of a therapeutic agent and an additive, e.g., the layer includes only the therapeutic agent and the additive, without any other materially significant components. In some embodiments, the device may optionally include an adherent layer. For example, as shown in the embodiment depicted in FIG. 4B, the balloon 12 is coated with an adherent layer 22. A layer 24 that includes a therapeutic agent and an additive is overlying the adherent layer. The adherent layer, which is a separate layer underlying the drug coating layer, improves the adherence of the drug coating layer to the exterior surface of the medical device and protects coating integrity. For example, if drug and additive differ in their adherence to the balloon, the adherent layer can prevent differential loss of components and maintain drug-to-additive ratio in the coating during transit to a target site for therapeutic intervention. Furthermore, the adherent layer can function to facilitate rapid release of coating layer components off the device surface upon contact with tissues at the target site. In other embodiments, the device can include a top layer. For example, as shown in the embodiment depicted in FIG. 4C, the balloon 12 is coated with an adherent layer 22, a layer 26 that includes a therapeutic agent and an additive overlying the adherent layer, and a top layer 28. The top layer can reduce loss of the drug layer before it is brought into contact with target tissues, for example during transit of the balloon 12 to the site of therapeutic intervention or during the first moments of inflation of balloon 12 before coating layer 20 is pressed into direct contact with target tissue.
Therapeutic Agent.

The balloon catheter can include a coating layer overlaying an exterior surface of the balloon. The coating layer can include one or more additives and initial drug load of a therapeutic agent. The coating layer can be a single layer, or the coating layer can include two or more layers. The coating layer can include one therapeutic agent or more than one therapeutic agent. The therapeutic agent can be in direct contact with the exterior of the balloon, of the balloon can include a coating between the therapeutic agent and the exterior of the balloon, such as a layer including one or more additives.

The therapeutic agent can be a hydrophobic therapeutic agent, an anti-inflammatory drug, and/or an anti-proliferative drug. The therapeutic agent can be of any suitable physical state, such as molecular distribution, crystal forms, or cluster forms. The therapeutic agent can include a lipophilic substantially water insoluble drug, such as paclitaxel, rapamycin, daunorubicin, doxorubicin, lapachone, vitamin D2 and D3, and analogues and derivatives thereof. The therapeutic agent can include paclitaxel, docetaxel, taxol, rapamycin, sirolimus, zotarolimus, everolimus, tacrolimus, mTOR inhibitors (i.e., a class of drugs that inhibit the mechanistic target of rapamycin), an analogue thereof (i.e., an analogue of any member of the list), or a combination thereof. The therapeutic agent can be in any suitable form, such as crystalline, partially crystalline, amorphous, partially amorphous, or a combination thereof. In some embodiments, the therapeutic agent can have a particle size of 0.2 microns to 10 microns, or preferably 0.5 microns to 5 microns. In some embodiments, the therapeutic agent is at least 75 wt % crystalline or at least 90 wt % crystalline. In another embodiment the drug is substantially amorphous with little or no molecular orientation. Techniques to determine if the a drug is crystalline or amorphous include power x-ray diffraction (pXRD), modulated differential scanning calorimetry (mDSC), or confocal raman spectroscopy.

In some embodiments, the one or more additives can partially or fully encapsulate the therapeutic agent. For example, the size of particles of the therapeutic agent encapsulated by the one or more additives can be 0.7 microns to 15 microns.

The therapeutic agent can include budesonide, flunisolide, triamcinolone, beclomethasone, fluticasone, mometasone, mometasone furoate, dexamethasone, hydrocortisone, methylprednisolone, prednisone, cortisone, betamethasone, triamcinolone acetonide, or a combination thereof. The therapeutic agent can include a bronchodilator or a vasoconstrictor. The therapeutic agent can include terbutaline, albuterol, ipratropium, pirbuterol, epinephrine, salmeterol, levalbuterol, formoterol, or a combination thereof.

In various aspects, a combination of therapeutic agents can be used. Various drug combinations can have additive effects because of different therapeutic mechanisms. For example, the therapeutic agent can include a combination of paclitaxel and rapamycin, a combination of paclitaxel and active vitamin D, a combination of paclitaxel and lapachone, a combination of rapamycin and active vitamin D, a combination of rapamycin and lapachone, or a combination thereof. In various aspects, due to additive effects of the therapeutic agents, the dose of one or more therapeutic agents can be reduced, reducing or preventing complications caused by a higher dose of one or more of the therapeutic agents.

In various aspects, the therapeutic agent is a polymer-encapsulated drug particle.
Additive.

The balloon catheter can include a coating layer overlaying an exterior surface of the balloon. The coating layer can include one or more additives and initial drug load of a therapeutic agent.

The one or more additives can include one or more water insoluble additives. The one or more additives can include one or more slightly water insoluble and/or partially water insoluble additives. The one or more additives can include one or more water soluble additives. The one or more additives can include: a) one or more water soluble additives, and b) one or more water insoluble or partially water insoluble additives.

The one or more additives can be chosen from pentaerythritol ethoxylate, pentaerythritol propoxylate, pentaerythritol propoxylate/ethoxylate, N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, sphingosine, polyethylene glycol (PEG) caprylic/capric diglycerides, PEG-8 caprylic/capric glycerides, PEG caprylate, PEG-8 caprylate, PEG caprate, PEG caproate, glyceryl monocaprylate, glyceryl monocaprate, glyceryl monocaproate, mono-laurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl) urea, N,N'-bis(hydroxymethyl) urea, glycerol ethoxylate, glycerol propoxylate, trimethylolpropane ethoxylate, pentaerythritol, dipentaerythritol, crown ether, 18-crown-6,15-crown-5,12-crown-4, and combinations thereof. The one or more additives can include pentaerythritol ethoxylate, pentaerythritol propoxylate, or a combination thereof. The one or more additives can include butylated hydroxytoluene (BHT), butylated hydroxyanisole (BHA), a derivative thereof, and/or a combination thereof. The one or more additives can include a polymer. In various aspects, the therapeutic agent can include a polymer-encapsulated drug particle.

The coating layer overlying the exterior of the balloon can include one or more water-soluble additives (e.g., a water-soluble first additive, a water-soluble second additive, and a water-soluble third additive). The water-soluble additive can include a first water soluble additive that is a surfactant such as a PEG sorbitan monolaurate, a PEG sorbitan monooleate, or a combination thereof. The water-soluble additive can include a second water-soluble additive that is a chemical compound with one or more moieties that are hydroxyl, amine, carbonyl, carboxyl, or ester, such as sorbitol, sorbitan, xylitol, gluconolactone, or a combination thereof. The coating layer can include both the first water-soluble additive and the second water-soluble additive. In some embodiments, the distal end of the balloon can be free of the therapeutic agent.

In some embodiments, the additive is at least one of a surfactant and a chemical compound.

In some embodiments the coating with a therapeutic agent and has at least one water soluble component and at least one water insoluble component or partially water-soluble component and the coating releases off the balloon into aqueous media in less than 30 seconds with no agglomerated particles or individual particles greater than 20 μm. In some embodiments the coating released has particles or agglomerated particles less than 10 μm, or preferably less than 5 μm particles.

In some embodiments, the one or more additives can enhance release of the therapeutic agent off the balloon. The additive can enhance penetration and absorption of the therapeutic agent in tissue. The additive can have a water and ethanol solubility of at least 1 mg/mL and the therapeutic agent can be water-insoluble.

The coating overlying the surface of the balloon can include a therapeutic agent and at least two additives, wherein each of the additives includes a hydrophilic part and a drug affinity part, wherein the drug affinity part is at least one of a hydrophobic part, a part that has an affinity to the therapeutic agent by hydrogen bonding, and a part that has an affinity to the therapeutic agent by van der Waals interactions, and wherein each additive is soluble in polar organic solvent and is soluble in water. In one aspect of this embodiment, the polar organic solvent is chosen from methanol, ethanol, isopropanol, acetone, dimethylformide, tetrahydrofuran, methylethyl ketone, dimethylsulfoxide, acetonitrile, ethyl acetate, and chloroform and mixtures of these polar organic solvents with water. In another aspect of this embodiment, the balloon further includes a top layer overlying the surface of the layer overlying the exterior surface of the balloon to reduce loss of drug during transit through a body to the target tissue.

The one or more additives can facilitate rapid drug elution and superior permeation of drug into tissues at a stricture or stenosis site. Thus, coatings according to embodiments of the present invention provide an enhanced rate and/or extent of absorption of the antiproliferative therapeutic agent in airway strictures or stenosis. In embodiments of the present invention, the coated device delivers antiproliferative therapeutic agent to the airway stricture or stenosis during a very brief deployment time of less than 10 minutes, less than 2 minutes, and reduces re-narrowing and reoccurring of the strictures of a nonvascular body lumen.

The additive, such a water-insoluble or slightly or partial water-insoluble additive, can be chosen from cholesteryl acetate, cholesteryl phenylacetate, cholesteryl laurate, cholesteryl palmitate, cholesteryl stearate, cholesteryl n-valerate, cholesteryl benzoate, cholesteryl heptylate, cholesteryl decylate, cholesteryl caproate, cholesteryl oleate, cholesteryl oleyl carbonate, cholesteryl linoleate, cholesteryl pelargonate, cholesteryl erucate, cholesteryl caprylate, 5-α-cholestane, 5α-cholestan-3-one. The water-insoluble or slightly or partial water-insoluble first additive with alkyl fatty group is chosen from alkyl glyceryl ethers, monoglycerides of C8-C12 fatty acids, alkyl alcohol, alkyl ether, alkyl ester, caprylic acid, monocaprilin, capric acid, monocaprin, lauric acid, dodecyl glycerol, butanoic acid, hexanoic acid, octanoic acid, decanoic acid, dodecanoic acid, tetradecanoic acid, hexadecanoic acid, octadecanoic acid, octadecatrienoic acid, eicosanoic acid, eicosenoic acid, eicosatetraenoic acid, eicosapentaenoic acid, docosahexaenoic acid, tocotrienol, butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, natural or synthetic phospholipids, mono-, di-, or triacylglycerols, cardiolipin, phosphatidylglycerol, phosphatidic acid, phosphatidylcholine, alpha tocopherol, phosphatidylethanolamine, sphingomyelin, phosphatidylserine, phosphatidylinositol, dimyristoylphosphatidylcholine, dioleoylphosphatidylcholine, dipalmitoylphosphatidylcholine, distearoylphosphatidylcholine, phosphatidylethanolamines phosphatidylglycerols, sphingolipids, prostaglandins, gangliosides, neobee, niosomes, and derivatives. and combinations thereof.

The additive, such as a water soluble second additive, can include polyethylene glycol (PEG)-cholesteryl sebacate, polyoxyethanyl α-tocopheryl sebacate, methylated polyethylene glycol cholesterol (mPEG cholesterol), polyethylene glycol cholesterol, PEG amide ester cholesterol, PEG amide ether cholesterol, mPEG amide ester cholesterol, PEG amide ether cholesterol, DSPE-PEG-cholesterol, PEGylated phospholipid, methylated PEGylated phospholipid, PEG caprylic/capric diglycerides, PEG8 caprylic/capric glycerides, PEG caprylate, PEG caprate, PEG caproate, PEG-20 sorbitan monolaurate (Tween-20), PEG-20 sorbitan monopalmitate (Tween-40), PEG-20 sorbitan monostearate (Tween-60), PEG-20 sorbitan monooleate (Tween-80), PEG laurate, PEG oleate, PEG stearate, PEG glyceryl laurate, and PEG-30 glyceryl oleate.

In some embodiments, the one or more additives includes a first additive including a water-insoluble or slightly or partial water-insoluble additive including at least one alkyl fatty group or cholesteryl group with a molecular weight of 50 to 750. One or more of the additives, such as a water insoluble additive in the coating, can have a lower melting temperature than its pure form. One or more of the additives, such as a water insoluble additive in the coating, can have a lower crystallinity than that of its pure form. One or more of the additives, such as a water-soluble additive can be more hydrophilic or more water soluble than a water-insoluble or slightly or partial water-insoluble additive in the coating. A water-soluble additive can include a polyethylene glycol ($-(CH_2CH_2O)-$) unit with a molecular weight in the range of 750 to 100,000, or 750 to 50,000, or 750 to 10,000.

EXAMPLES

Figure 5:
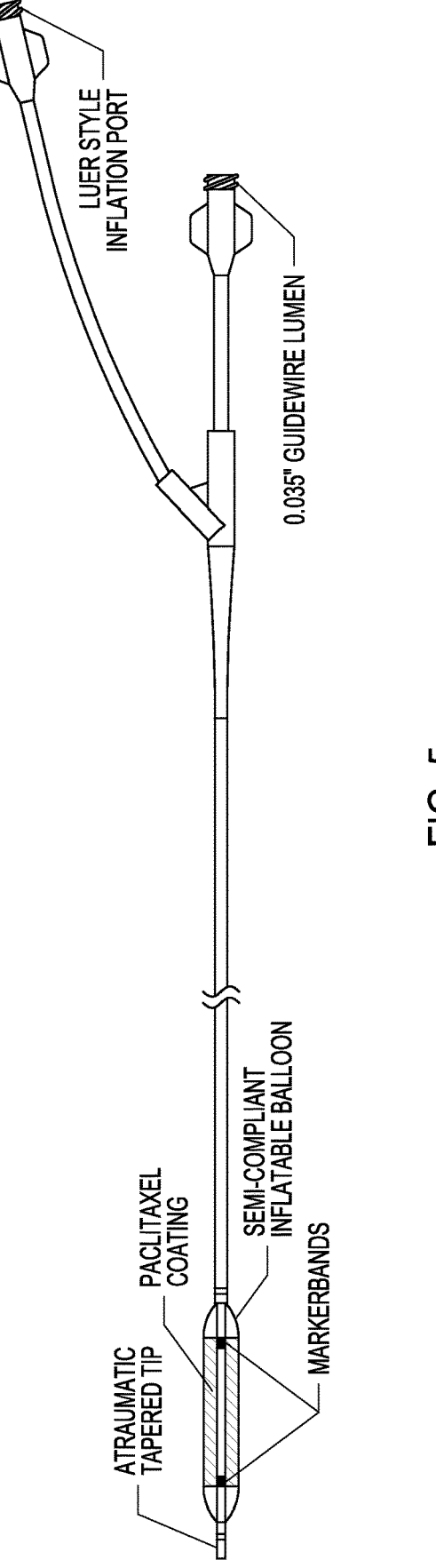
FIG. 5 illustrates a drug-coated balloon catheter on a guidewire, in accordance with various embodiments.

The device used was a 0.035" guidewire compatible over-the-wire catheter with a tapered atraumatic tip. The distal end of the catheter had a semi-compliant inflatable balloon coated with a proprietary coating containing the drug paclitaxel and carriers that facilitates the drug's transfer to the airway wall upon inflation. The drug coating covers only the balloon body. The device had two radiopaque marker bands that indicated the drug coated working length of the balloon under fluoroscopy. The device was provided sterile and is intended for single use only. FIG. 5 illustrates the device, and Table 5 summarizes the specifications of the device.

peutic systemic injectable dose of 333 mg paclitaxel/adult man (assumes dosing of 175 mg paclitaxel/$m^2$ and 1.9 $m^2$ surface area for a man). The dose density for each catheter is 3.5 μg paclitaxel/$mm^2$ of balloon surface. Table 6 details the amount of drug delivered by balloon size.

TABLE 6

| Nominal Paclitaxel Dose per Balloon (mg). | |
| --- | --- |
| BALLOON | Drug Dose (mg Paclitaxel) |
| 8 × 30 | 2.6 |
| 10 × 30 | 3.3 |
| 12 × 30 | 4.0 |
| 14 × 30 | 4.6 |
| 12 × 65 | 8.6 |
| 15 × 65 | 10.7 |
| 18 × 65 | 12.9 |

Two preclinical studies are described in Examples 1 and 2. A total of 10 sheep have been treated with the device and to analyze product design feasibility and procedural safety in these anatomies.

Acute Preclinical Study #1 was an acute study conducted on one live sheep to determine acute drug transfer and further refine bronchoscope access techniques, device compatibility, and tissue collection techniques.

Chronic Preclinical Study #2 was a chronic (28 day) study with nine sheep to assess gross pathology of the treatment sites, pharmacokinetics of plasma, treatment sites, and organs, and assess overall animal health during the 28 day in-life phase of the study. Animal safety, device performance, and procedural information was gathered such as overall health of the animals, weight gain over time, treatment site, plasma, downstream, and organ paclitaxel pharmacokinetics, gross pathology, and histology. Results and conclusions from these studies are summarized in Examples 1 and 2 herein. In Examples 1 and 2, the drug-coated balloons were soaked prior to treatment to activate the drug coating.

Examples 3 and 4 describe acute and chronic studies on the nasal tissue with 5 live sheep. In Examples 3 and 4, the

TABLE 5

| BALLOON | DRUG DOSE (Paclitaxel) (mg) | NOMINAL BALLOON OD [mm] | NOMINAL BALLOON LENGTH [mm] | MIN RATED BURST (ATM) | Shaft Length | Bronchoscope Compatibility |
| --- | --- | --- | --- | --- | --- | --- |
| 8 × 30 | 2.6 | 8.0 @ 6 ATM | 30.0 | 12 | 75 cm | ≥2.8 mm Working Channel |
| 10 × 30 | 3.3 | 10.0 @ 6 ATM | 30.0 | 10 | | |
| 12 × 30 | 4.0 | 12.0 @ 6 ATM | 30.0 | 8 | | |
| 14 × 30 | 4.6 | 14.0 @ 6 ATM | 30.0 | 8 | | |
| 12 × 65 | 8.6 | 12.0 @ 3 ATM | 65.0 | 7 | 240 cm | ≤60 cm Total Length |
| 15 × 65 | 10.7 | 15.0 @ 3 ATM | 65.0 | 6 | | |
| 18 × 65 | 12.9 | 18.0 @ 3 ATM | 65.0 | 5 | | |

The amount of drug applied to the surface of the largest DCB (12.9 mg for the 18×65 DCB) is anticipated to be approximately 30 times lower than a typical chemotheranasal treatment sites were flushed with a solution that was saline or water, the balloon catheter was inserted to the nasal treatment site, the balloon catheter was soaked at the site to hydrate and activate the drug coating at the site of treatment, prior to inflation. The drug coated catheters were inflated at the target site for 3-5 minutes.

Example 1. Acute Preclinical Study #1

Figure 6:
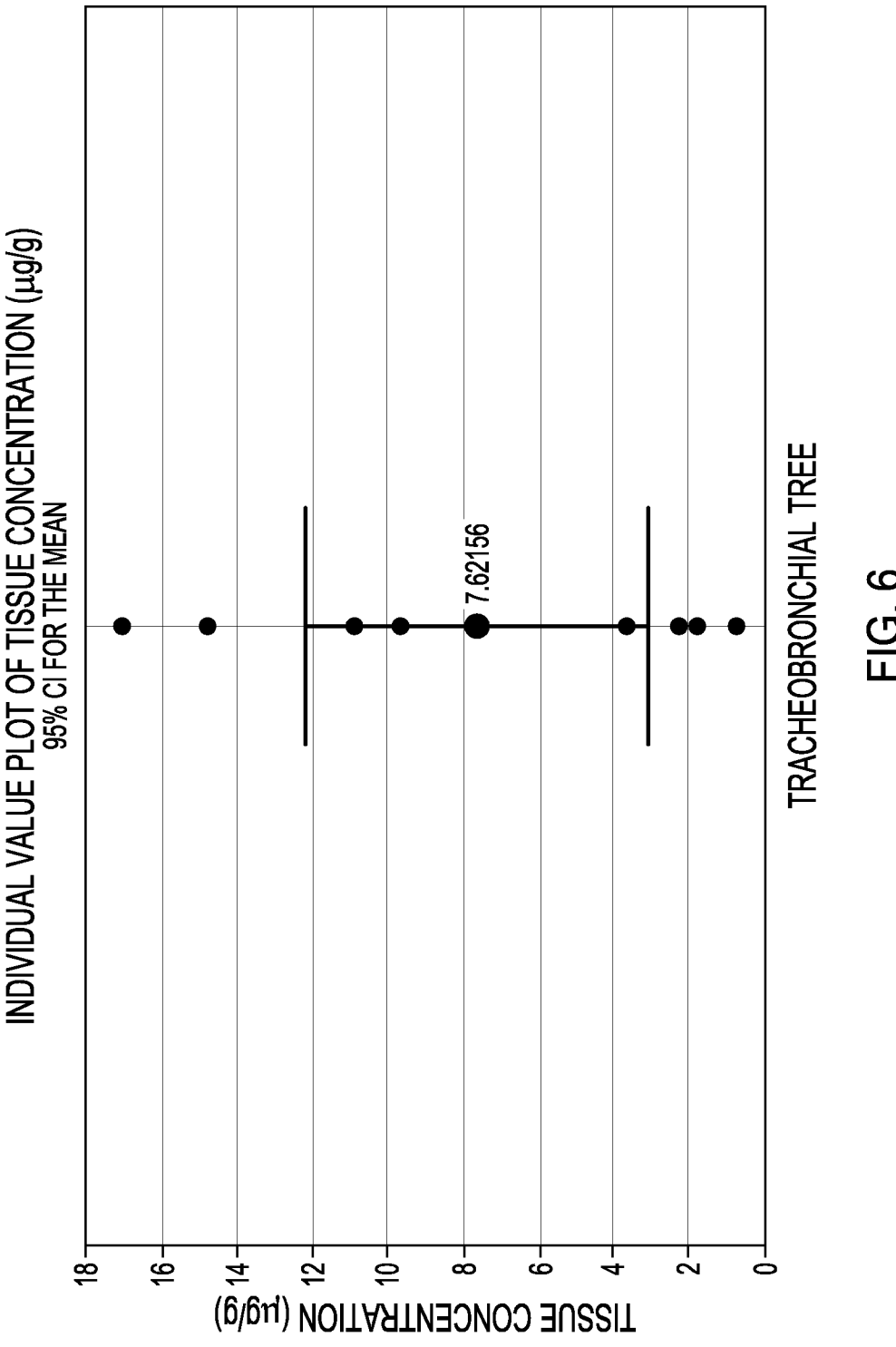
FIG. 6 illustrates 1-h paclitaxel concentration in treated tissues, in accordance with various embodiments.
Figure 7:
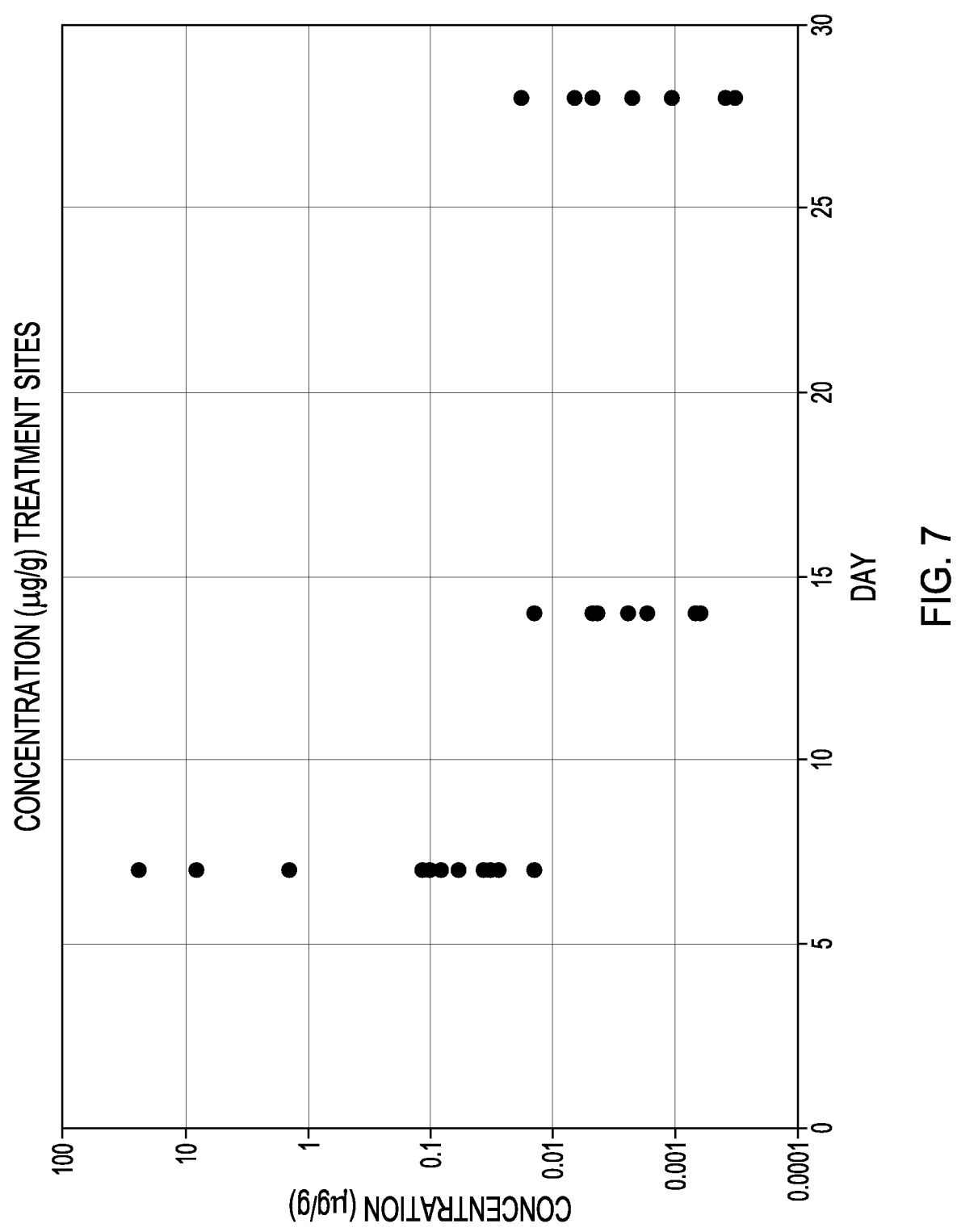
FIG. 7 illustrates concentration of paclitaxel versus time, in accordance with various embodiments.

Acute drug transfer was measured in Acute Preclinical Study #1. FIG. 6 illustrates 1-hour paclitaxel drug concentration in the treated tissues. FIG. 6 demonstrates that the body before inserting the balloon catheter to the target sites in tracheal and bronchial airways. The target sites in tracheal and bronchial airways were not flushed. At 28 days there are low levels of paclitaxel in the tissue of the treatment site. At the treated tissue, the $T_{max}$ was at one hour, $C_{max}$ was 6.2 μg/g, and AUC was 52.3 μg/day/g. At the day 28, the average tissue drug level was 3.4 ng/g. The data shown in FIG. 7 is shown in Table 7.

TABLE 7

| Treat-ment Site | Time-point (d) | Tissue | Part of Lung | Balloon Size | Label Claim (ug) | Pre-Soak Time (s) | Inflation Time (min) | Total PTX (ug) | Percent of Label Claim | Tissue Weights (g) | Concen-tration (ng/g) | Total Pacli-taxel (ng) | Concen-tration (μg/g) |
|---|---|---|---|---|---|---|---|---|---|---|---|---|---|
| Lungs | 7 | Balloon 1 | Bronchi | 10 × 30 | 3299 | 90 | 3 | 2029.9 | 62% | 0.46938 | 27.9 | 13.1 | 0.0279 |
| Lungs | 7 | Balloon 10 | Trachea | 18 × 65 | 12865 | 90 | 2 | 7528.6 | 59% | 12.39149 | 30 | 372 | 0.03 |
| Lungs | 7 | Balloon 11 | Trachea | 18 × 65 | 12865 | 90 | 2 | 5949.6 | 46% | 12.79954 | 30.4 | 389 | 0.0304 |
| Lungs | 7 | Balloon 12a | Trachea | 18 × 65 | 12865 | 90 | 2 | 5308.5 | 41% | 8.82269 | 35.4 | 312 | 0.0354 |
| Lungs | 7 | Balloon 2 | Bronchi | 12 × 30 | 3958 | 90 | 3 | 2775 | 70% | 0.71741 | 99.2 | 71.2 | 0.0992 |
| Lungs | 7 | Balloon 3 | Bronchi | 14 × 30 | 4618 | 90 | 3 | 3207.3 | 69% | 1.60067 | 23600 | 37800 | 23.6 |
| Lungs | 7 | Balloon 4 | Bronchi | 15 × 55 | 9072 | 90 | 3 | 5073.4 | 56% | 4.7735 | 1420 | 6780 | 1.42 |
| Lungs | 7 | Balloon 5 | Bronchi | 12 × 30 | 3958 | 90 | 3 | 2700.2 | 68% | 2.29622 | 64.1 | 147 | 0.0641 |
| Lungs | 7 | Balloon 6 | Bronchi | 12 × 30 | 3958 | 90 | 3 | 1798 | 45% | 1.85775 | 8060 | 15000 | 8.06 |
| Lungs | 7 | Balloon 7 | Bronchi | 14 × 30 | 4618 | 90 | 3 | 2831.8 | 61% | 1.09789 | 81.7 | 89.7 | 0.0817 |
| Lungs | 7 | Balloon 8 | Bronchi | 10 × 30 | 3299 | 90 | 3 | 1014 | 31% | 1.91407 | 23600 | 45200 | 23.6 |
| Lungs | 7 | Balloon 9 | Bronchi | 18 × 65 | 12865 | 90 | 3 | 6884.7 | 54% | 4.23841 | 113 | 479 | 0.113 |
| Lungs | 14 | Balloon 1 | Bronchi | 10 × 30 | 3299 | 90 | 3 | 1834.3 | 56% | 2.47881 | 1.75 | 4.34 | 0.00175 |
| Lungs | 14 | Balloon 10 | Trachea | 18 × 55 | 10886 | 90 | 2 | 8490.3 | 78% | 13.37364 | 0.657 | 8.79 | 0.000657 |
| Lungs | 14 | Balloon 2 | Bronchi | 10 × 30 | 3299 | 90 | 3 | 2509.2 | 76% | 1.35561 | 0 | 0 | 0 |
| Lungs | 14 | Balloon 3 | Bronchi | 8 × 30 | 2639 | 90 | 3 | 1796.2 | 68% | 1.4749 | 14.4 | 21.2 | 0.0144 |
| Lungs | 14 | Balloon 4 | Bronchi | 18 × 55 | 10886 | 90 | 3 | 8543 | 78% | 5.32653 | 4.46 | 23.8 | 0.00446 |
| Lungs | 14 | Balloon 5 | Bronchi | 10 × 30 | 3299 | 90 | 3 | 2543.1 | 77% | 3.30574 | 0.707 | 2.34 | 0.000707 |
| Lungs | 14 | Balloon 6 | Bronchi | 10 × 30 | 3299 | 90 | 3 | 2653 | 80% | 2.02264 | 0 | 0 | 0 |
| Lungs | 14 | Balloon 7 | Bronchi | 8 × 30 | 2639 | 90 | 3 | 1856.8 | 70% | 1.72604 | 4.88 | 8.42 | 0.00488 |
| Lungs | 14 | Balloon 8 | Bronchi | 18 × 55 | 10886 | 90 | 3 | 9312.8 | 86% | 4.60936 | 0 | 0 | 0 |
| Lungs | 14 | Balloon 9 | Trachea | 18 × 65 | 12865 | 90 | 2 | 5564.4 | 43% | 13.98751 | 2.47 | 34.5 | 0.00247 |
| Lungs | 28 | Balloon 1 | Bronchi | 10 × 30 | 3299 | 90 | 3 | 2489.9 | 75% | 1.76904 | 0.331 | 0.586 | 0.000331 |
| Lungs | 28 | Balloon 10 | Trachea | 18 × 65 | 12865 | 90 | 2 | 8503 | 66% | 13.69496 | 2.24 | 30.7 | 0.00224 |
| Lungs | 28 | Balloon 2 | Bronchi | 8 × 30 | 2639 | 90 | 3 | 2259.5 | 86% | 0.98894 | 0 | 0 | 0 |
| Lungs | 28 | Balloon 3 | Bronchi | 14 × 30 | 4618 | 90 | 3 | 3020.8 | 65% | 1.01679 | 0.387 | 0.393 | 0.000387 |
| Lungs | 28 | Balloon 4 | Bronchi | 15 × 55 | 9072 | 90 | 3 | 5940 | 65% | 5.63988 | 18.2 | 103 | 0.0182 |
| Lungs | 28 | Balloon 5 | Bronchi | 12 × 30 | 3958 | 90 | 3 | 2378.8 | 60% | 2.20572 | 0 | 0 | 0 |
| Lungs | 28 | Balloon 6 | Bronchi | 8 × 30 | 2639 | 90 | 3 | 1812.5 | 69% | 1.19696 | 0 | 0 | 0 |
| Lungs | 28 | Balloon 7 | Bronchi | 15 × 55 | 9072 | 90 | 3 | 6714.1 | 74% | 5.29188 | 4.95 | 26.2 | 0.00495 |
| Lungs | 28 | Balloon 8 | Trachea | 18 × 65 | 12865 | 90 | 2 | 6704 | 52% | 12.16796 | 1.08 | 13.1 | 0.00108 |
| Lungs | 28 | Balloon 9 | Bronchi | 8 × 30 | 2639 | 90 | 3 | 1205.8 | 46% | 1.42766 | 6.95 | 9.92 | 0.00695 | paclitaxel can be successfully delivered to the trachea and bronchi on a drug coated balloon.

Example 2. Chronic Preclinical Study #2

Overall Animal Health (Moribundity)

All assessments suggested that animals remained in good general health throughout the duration of the study. There were no deaths or major adverse events that affected animal health or welfare.

Treatment Site (Tracheobronchial) Paclitaxel Pharmacokinetics

Animals were terminated at 7, 14, and 28 days. At the time of termination, one animal from each timepoint was used for pharmacokinetic data and each treatment site in the tracheobronchial tree was excised and assayed via HPLC-MS for paclitaxel.

FIG. 7 indicates paclitaxel was delivered to the tissue at the time of treatment and then the paclitaxel concentration decreases with increased time passed. In Examples 1 and 2, the drug coated balloon catheters were soaked and/or hydrated in water or saline solutions for 90 seconds outside Local and Non-Target Organ Histopathology at 28 Days FIG. 12A illustrates a SEM image of a test article treatment site 28 days after treatment. FIG. 12B illustrates SEM image of a control article treatment site after 28 days. At the treatment sites there was no thrombosis, no loss of epithelium, no submucosal hemorrhage, and no necrosis. The airway lumen remained patent with no airway wall collapse. As is expected after treatment with paclitaxel, submucosal inflammation, smooth muscle loss, submucosal fibrosis, and adventitial fibrosis were more common in the test animal than in the control animal. This aligns with the healing responses after exposure to paclitaxel. Under SEM, airways from test animals were >90% covered with ciliated epithelial cells at 28 days versus 51%-90% coverage in airways from control animals.

There were no microscopic morphological abnormalities observed in any of the heart, liver, spleen, kidney, or downstream lung tissue. All of these tissues appeared normal with no device related findings during bread loafing at gross necropsy and during histopathological assessment.

Overall Preclinical Study Conclusions

The following conclusions were drawn from the preclinical studies: Drug was successfully delivered to the treatment sites; drug concentration in the treatment sites decreases with time to low levels at 28 days; drug concentration within non-target organs is below the limit of quantitation at 28 days; drug concentration within the plasma is below the limit of quantitation at 7 days; there were no gross or histological observations of tracheobronchial tree toxicity arising from the treatments; in all test animals the tracheobronchial tree remained patent, and test animals were able to behave normally as shown by animal observations; and, the DCB performed acceptably and was able to be tracked, inflated, deflated, and withdrawn for all treatments. No major safety concerns have been raised in any of the preclinical studies performed to date with overdosing of 10-12 treatments per animal and no device-associated adverse reactions have been identified.

Acute Preclinical Study: Nasal Tissue.

Acute drug transfer in nasal tissue was measured using a 10×30 balloon. Table 8 shows 2-hour paclitaxel drug concentration in the treated tissues (the lateral nasal cavity (Tx 2)). Table 8 demonstrates that paclitaxel can be successfully delivered to nasal tissue on a drug coated balloon.

TABLE 8

| Drug transfer in nasal tissue after 2-hours. | | |
| --- | --- | --- |
| Tissue Weight (g) | Conc. (ng/g) | Total Paclitaxel (ng) |
| 0.4345 | 25200 | 10900 |
| 0.91718 | 7910 | 7250 |
| 0.44501 | 7000 | 3120 |
| 1.29058 | 17000 | 21900 |
| 0.65835 | 14300 | 9410 |
| 1.2294 | 9930 | 12200 |

Chronic Preclinical Study: Nasal Tissue.

Table 9 shows results of the chronic preclinical study. Nasal Tx 1 was the superior nasal cavity, Nasal Tx 2 was the lateral nasal cavity, and Nasal Tx 3 was anterior and inferior nasal cavity.

art, and that such modifications and variations are considered to be within the scope of embodiments of the present invention.

Exemplary Embodiments

The following exemplary embodiments are provided, the numbering of which is not to be construed as designating levels of importance:

Embodiment 1 provides a method of treatment of a recurring airway stricture or stenosis in an airway body lumen, the method comprising:

inserting a scope and a balloon catheter into a target site at the recurring airway stricture or stenosis in the airway body lumen, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site.

Embodiment 2 provides the method of Embodiment 1, further comprising damaging, dilating, and/or removing the stricture or stenosis at the target site in the body lumen prior to the insertion of the scope and balloon catheter into the target site.

Embodiment 3 provides the method of Embodiment 2, wherein the damaging, dilating, and/or removing of the stricture or stenosis inserting a predilation balloon into the

TABLE 9

| | | | | | | | | Treat-ment | Treat-ment | | Treat-ment | | |
| --- | --- | --- | --- | --- | --- | --- | --- | --- | --- | --- | --- | --- | --- |
| | | | | Tissue | | Total Pacli- | | Site | Site | Infla-tion | Area | DCB | Stretch |
| Tissue | | | | Weight | Conc. | taxel | DCB | Width | Height | Pressure | Calc'd | Area | Ratio |
| Type | Term | Subject | Sample ID | (g) | (ng/g) | (ng) | Size | (mm) | (mm) | (atm) | (mm²) | (mm2) | (%) |
| Nasal Tissue | 14 d | 22S0154 | RT Nasal Tx 1 | 0.42982 | 11.2 | 4.81 | 10 × 30 | 4 | 9 | | 28.27 | 78.54 | 177.8 |
| Nasal Tissue | 28 d | 22S0218 | LT Nasal Tx 1 | 0.32844 | 0.962 | 0.316 | 8 × 30 | 3 | 8 | | 18.85 | 50.27 | 166.7 |
| Nasal Tissue | 28 d | 22S0218 | RT Nasal Tx 2 | 0.45434 | 0.469 | 0.213 | 8 × 30 | 3 | 6 | | 14.14 | 50.27 | 255.6 |
| Nasal Tissue | 7 d | 22S0222 | LT Nasal Tx 3 | 0.56979 | 11.4 | 6.50 | 12 × 30 | 5 | 8 | 8 | 31.42 | 113.10 | 260.0 |
| Nasal Tissue | 7 d | 22S0222 | RT Nasal Tx 1 | 0.44883 | 0.448 | 0.201 | 6 × 30 | 3 | 6 | 6 | 14.14 | 28.27 | 100.0 |

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the body lumen at the target site, inflating the predilation balloon, and removing the predilation balloon prior to inserting the drug coated balloon catheter.

Embodiment 4 provides the method of any one of Embodiments 2-3, wherein the damaging, dilating, and/or removing comprises surgical removal, electrocautery, laser ablation, cryoablation, radiofrequency ablation, mechanical debulking, rigid bronchoscopy dilation, knife-cutting, direct vision internal stricturotomy, use of an uncoated balloon to dilate the stricture or stenosis, or a combination thereof.

Embodiment 5 provides the method of any one of Embodiments 1-4, further comprising, prior to the inflating, flushing the target site with a flushing composition comprising water and/or saline, and hydrating and/or soaking the coating in the flushing composition at the target site, or hydrating and/or soaking the coating in saline, water, and/or natural fluids native to the body lumen that are not externally added, wherein the hydrating and/or soaking is performed outside the body, in the body lumen while the balloon catheter is en route to the target site, at the target site, or a combination thereof, or a combination thereof.

Embodiment 6 provides the method of Embodiment 5 wherein the hydrating and/or soaking is performed for 0.1 minutes to 5 minutes.

Embodiment 7 provides the method of any one of Embodiments 5-6, wherein the flushing is performed prior to and/or during the insertion of the scope and balloon catheter into the target site.

Embodiment 8 provides the method of any one of Embodiments 5-7, further comprising flushing the target site with a flushing composition comprising water and/or saline, and performing the hydrating and/or soaking of the coating in the flushing composition at the target site; or performing the hydrating and/or soaking of the drug coating outside the body with a flushing composition comprising water and/or saline prior to inserting the drug coated balloon into the target site, and optionally wherein the method is free of flushing at the target site.

Embodiment 9 provides the method of any one of Embodiments 1-8, wherein the one or more additives comprise one or more water insoluble additives.

Embodiment 10 provides the method of any one of Embodiments 1-9, wherein the one or more additives comprise one or more slightly water insoluble and/or partially water insoluble additives.

Embodiment 11 provides the method of any one of Embodiments 1-10, wherein the one or more additives comprise one or more water soluble additives.

Embodiment 12 provides the method of any one of Embodiments 1-11, wherein the one or more additives comprise:

one or more water soluble additives, and one or more water insoluble or partially water insoluble additives.

Embodiment 13 provides the method of any one of Embodiments 1-12, wherein the one or more additives are chosen from pentaerythritol ethoxylate, pentaerythritol propoxylate, pentaerythritol propoxylate/ethoxylate, N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, sphingosine, polyethylene glycol (PEG) caprylic/capric diglycerides, PEG-8 caprylic/capric glycerides, PEG caprylate, PEG-8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl) urea, N,N'-bis(hydroxymethyl)

urea, glycerol ethoxylate, glycerol propoxylate, trimethylolpropane ethoxylate, pentaerythritol, dipentaerythritol, crown ether, 18-crown-6,15-crown-5,12-crown-4, butylated hydroxytoluene (BHT), butylated hydroxyanisole (BHA), a derivative thereof, and combinations thereof.

Embodiment 14 provides the method of any one of Embodiments 1-13, wherein the one or more additives comprise pentaerythritol ethoxylate, pentaerythritol propoxylate, or a combination thereof.

Embodiment 15 provides the method of any one of Embodiments 1-14, wherein the balloon has a main diameter that is a nominal inflated diameter of at least 1 mm, or at least 15 mm, or at least 20 mm, or at least 30 mm, or at least 35 mm.

Embodiment 16 provides the method of any one of Embodiments 1-15, wherein the balloon catheter comprises the elongated balloon and is free of other balloons.

Embodiment 17 provides the method of any one of Embodiments 1-16, wherein the balloon catheter comprises more than one balloon.

Embodiment 18 provides the method of any one of Embodiments 1-17, wherein the balloon is substantially free of neck sections between a proximal and a distal end of the balloon.

Embodiment 19 provides the method of any one of Embodiments 1-18, wherein the balloon comprises at least one neck section on the balloon comprising a smaller diameter than a main diameter of the balloon when the balloon is inflated, the at least one neck section dividing the balloon into at least two main sections each having a diameter.

Embodiment 20 provides the method of Embodiment 19, wherein the diameter of the at least two main sections is equal to the main diameter of the elongated balloon, or the at least one neck section has a diameter that is about 5% to about 99% of the diameter of at least one of the at least two main sections.

Embodiment 21 provides the method of any one of Embodiments 19-20, wherein the at least one neck section has a diameter that is independently about 5 mm to about 40 mm.

Embodiment 22 provides the method of any one of Embodiments 19-21, wherein the diameter of the at least one neck section is substantially static during inflation of the balloon.

Embodiment 23 provides the method of any one of Embodiments 19-22, wherein the at least one neck section comprises a substantially nonelastic portion of the balloon, a reinforced portion of the balloon, or a combination thereof.

Embodiment 24 provides the method of any one of Embodiments 19-23, wherein the at least one neck section comprises an inelastic material around a circumference of the neck section.

Embodiment 25 provides the method of Embodiment 24, wherein the inelastic material comprises ultra high molecular weight polyethylene, a nylon, a polyamide, or a combination thereof Embodiment 26 provides the method of any one of Embodiments 19-25, wherein the diameter (e.g., inflated diameter) of the at least two main sections are about 5 mm to about 45 mm.

Embodiment 27 provides the method of any one of Embodiments 19-26, wherein the at least one neck section is about 1% to about 50% of the balloon length.

Embodiment 28 provides the method of any one of Embodiments 19-27, wherein the at least one neck section is one neck section and the balloon is free of other neck sections.

Embodiment 29 provides the method of any one of Embodiments 19-28, wherein the at least one neck section is two neck sections and the balloon is free of other neck sections.

Embodiment 30 provides the method of Embodiment 29, wherein the two neck sections have about the same diameter.

Embodiment 31 provides the method of any one of Embodiments 29-30, wherein one of the two neck sections have a smaller diameter than the other neck section.

Embodiment 32 provides the method of any one of Embodiments 29-31, wherein the two neck sections are symmetrically located with respect to the center of the balloon length.

Embodiment 33 provides the method of any one of Embodiments 29-32, wherein the balloon catheter comprises three of the main sections separated by the two neck sections.

Embodiment 34 provides the method of any one of Embodiments 29-33, wherein the at least one neck section is three neck sections, wherein the balloon is free of other neck sections.

Embodiment 35 provides the method of Embodiment 34, wherein the three neck sections are arranged to provide four of the main sections separated by the three neck sections.

Embodiment 36 provides the method of any one of Embodiments 1-35, wherein the elongated balloon has a length of about 20 mm to about 300 mm.

Embodiment 37 provides the method of any one of Embodiments 1-36, wherein the balloon catheter comprises a catheter shaft on a longitudinal end of the balloon, the catheter shaft comprising an interior lumen for delivery of a gas, liquid, or a combination thereof, to the balloon interior.

Embodiment 38 provides the method of any one of Embodiments 1-37, wherein the balloon catheter comprises an atraumatic Coude tip.

Embodiment 39 provides the method of any one of Embodiments 1-38, wherein after the deflation and withdrawal from the target site the balloon catheter comprises a residual drug amount that is less than 100 wt % of the initial drug load.

Embodiment 40 provides the method of any one of Embodiments 1-39, wherein after the deflation and withdrawal from the target site the balloon catheter comprises a residual drug amount that is about 70 wt % or less of the initial drug load.

Embodiment 41 provides the method of any one of Embodiments 1-40, wherein the initial drug load is from about 1 microgram to about 20 micrograms of the therapeutic agent per square millimeter of the balloon, measured when the balloon is at its nominal inflated diameter.

Embodiment 42 provides the method of any one of Embodiments 1-41, wherein the initial drug load is from about 2 to about 6 micrograms of the therapeutic agent per square millimeter of the balloon, measured when the balloon is at its nominal inflated diameter.

Embodiment 43 provides the method of any one of Embodiments 1-42, wherein a ratio by weight of the therapeutic agent in the coating layer to the total weight of the one or more additives in the coating layer is from about 0.05 to about 20.

Embodiment 44 provides the method of any one of Embodiments 1-43, wherein the ratio by weight of the therapeutic agent in the coating layer to the total weight of the one or more additives in the coating layer is from about 0.5 to about 8.

Embodiment 45 provides the method of any one of Embodiments 1-44, wherein the ratio by weight of the therapeutic agent in the coating layer to the total weight of the one or more additives in the coating layer is from about 2 to about 6.

Embodiment 46 provides the method of any one of Embodiments 1-45, wherein the balloon catheter has a stretch ratio of about 1.0 to about 20.

Embodiment 47 provides the method of any one of Embodiments 1-46, wherein the balloon catheter further comprises a sheath covering the elongated balloon, wherein the method comprises removing the sheath before the inflating.

Embodiment 48 provides the method of any one of Embodiments 1-47, wherein inserting the scope and the balloon catheter comprises inserting the balloon catheter through a lumen of the scope.

Embodiment 49 provides the method of any one of Embodiments 1-48, wherein inserting the scope and the balloon catheter comprises inserting the balloon catheter and the scope side-by-side.

Embodiment 50 provides the method of any one of Embodiments 1-49, comprising placing the scope and a proximal edge of the balloon at or near the target site.

Embodiment 51 provides the method of any one of Embodiments 1-50, wherein the scope is an endoscope, rhinolaryngoscope, rhinoscope, bronchoscope, cystoscope, or a combination thereof.

Embodiment 52 provides the method of any one of Embodiments 1-51, comprising visualizing positioning of the balloon catheter at the target site with the scope.

Embodiment 53 provides the method of any one of Embodiments 1-52, wherein the inflating is performed at least until the target site yields and is dilated.

Embodiment 54 provides the method of any one of Embodiments 1-53, wherein the inflating is performed such that the ratio of the inflation diameter to a normative body lumen diameter at the target site is about 1.0 to about 20.

Embodiment 55 provides the method of any one of Embodiments 1-54, wherein the inflating is performed such that the ratio of the inflation diameter to a normative body lumen diameter at the target site is about 1.0, 1.1, 1.2, or 1.31 to 10.

Embodiment 56 provides the method of any one of Embodiments 1-55, wherein the inflating is performed such that the balloon is inflated to a pressure that is equal to or greater than a nominal pressure of the balloon.

Embodiment 57 provides the method of any one of Embodiments 1-56, wherein the inflating is performed such that a stretch ratio of the inflated diameter of the balloon to a normative body lumen diameter at the target site is about 1.0 to about 20.

Embodiment 58 provides the method of any one of Embodiments 1-57, wherein the inflating is performed such that a stretch ratio of the inflated diameter of the balloon to a normative body lumen diameter at the target site is about 1.0, 1.1, 1.2, or 1.31 to 10.

Embodiment 59 provides the method of any one of Embodiments 1-58, wherein the inflating is performed such that a ratio of the inflation diameter to a normative body lumen diameter at the target site is about 1.0 to 20, and such that a stretch ratio of the inflated diameter of the balloon to a normative body lumen diameter at the target site of about 1.0 to about 20.

Embodiment 60 provides the method of any one of Embodiments 1-59, wherein the inflating is performed such that the balloon is inflated to a pressure greater than a nominal pressure of the balloon, and a nominal inflated diameter of the balloon is less than the inflated diameter.

Embodiment 61 provides the method of any one of Embodiments 1-60, wherein the inflating comprises observing pressure within the balloon.

Embodiment 62 provides the method of any one of Embodiments 1-61, wherein the inflating comprises inflating the balloon to a first pressure, allowing pressure within the balloon to stabilize while maintaining the first pressure in the balloon for a stabilization period, then resuming increasing pressure in the balloon until the inflation diameter is achieved.

Embodiment 63 provides the method of Embodiment 62, comprising visualizing the yielding and dilation of the target site with the scope.

Embodiment 64 provides the method of any one of Embodiments 1-63, comprising visualizing the inflating with the scope.

Embodiment 65 provides the method of any one of Embodiments 1-64, comprising maintaining the inflation diameter by keeping the balloon inflated for 1 minute to 7 days.

Embodiment 66 provides the method of any one of Embodiments 1-65, comprising maintaining the inflation diameter by keeping the balloon inflated for 1 minute to 1 day.

Embodiment 67 provides the method of any one of Embodiments 1-66, comprising maintaining the inflation diameter by keeping the balloon inflated for 1 minute to 10 minutes.

Embodiment 68 provides the method of any one of Embodiments 1-67, comprising maintaining the inflation diameter for a duration sufficient to release the drug into tissue of the target site and/or to prevent or reduce bleeding.

Embodiment 69 provides the method of any one of Embodiments 1-68, wherein the body lumen comprises a frontal sinus, ethmoid sinus, sphenoid sinus, maxillary sinus, nasal passage, supraglottis, glottis, subglottis, trachea, mainstem bronchus, *bronchus intermedius*, and/or a lobar bronchus.

Embodiment 70 provides the method of any one of Embodiments 1-69, wherein the recurring stricture or stenosis is idiopathic.

Embodiment 71 provides the method of any one of Embodiments 1-70, wherein the recurring stricture or stenosis is caused by a congenital condition, trauma, inflammation, post-intubation tracheal stenosis, post-tracheostomy tracheal restenosis, post-tuberculosis infection, transplant-related restenosis, repeated medication treatments, surgical removal, electrocautery, laser ablation, cryoablation, mechanical debulking, rigid bronchoscopic dilation, stent placement, and/or balloon dilation, and/or wherein the stricture or stenosis comprises CRS stenosis, CRSwNP stenosis, nasal stenosis, severe asthma, comorbidities of CRSwNP, comorbidities of severe asthma stenosis, subglottic stricture and/or stenosis, laryngostenosis, tracheal stenosis, bronchial stenosis, airway anastomotic stenosis, radiation induced airway stenosis, bronchial smooth muscle cells, IL-4, IL-5, IL-6, IL-13, IL-23, ILC2, mucus plug, goblet cells, fibrosis, cystic fibrosis, and/or one or more mucins.

Embodiment 72 provides the method of any one of Embodiments 1-71, wherein the airway stricture or stenosis comprises a tracheal and/or bronchial stricture or stenosis.

Embodiment 73 provides the method of any one of Embodiments 1-72, wherein the airway stricture or stenosis comprises chronic rhinosinusitis with nasal polyps (CRSwNP).

Embodiment 74 provides the method of any one of Embodiments 1-73, wherein the airway stricture or stenosis comprises laryngostenosis and/or subglottic stricture or stenosis.

Embodiment 75 provides the method of any one of Embodiments 1-74, wherein the airway stricture or stenosis is a stricture or stenosis induced by repeated medication treatments, intubation, tracheostomy, tuberculosis infection, surgical removal, electrocautery, laser ablation, cryoablation, mechanical debulking, rigid bronchoscopic dilation, stent placement, and/or balloon dilation.

Embodiment 76 provides the method of any one of Embodiments 1-75, further comprising damaging, dilating, and/or removing the stricture or stenosis at the target site in the body lumen prior to the insertion of the scope and balloon catheter into the target site, wherein:

the method is a method of treating chronic rhinosinusitis with nasal polyps (CRSwNP), wherein the airway stricture or stenosis is a structure or stenosis induced by CRSwNP.

Embodiment 77 provides the method of any one of Embodiments 1-76, further comprising damaging, dilating, and/or removing the stricture or stenosis at the target site in the body lumen prior to the insertion of the scope and balloon catheter into the target site, wherein:

the method is a method of treating laryngostenosis and/or subglottic stricture or stenosis, wherein the airway stricture or stenosis is a structure or stenosis induced by laryngostenosis and/or subglottic stricture or stenosis.

Embodiment 78 provides the method of any one of Embodiments 1-77, wherein the predilation balloon is substantially free of a drug coating.

Embodiment 79 provides a method of treatment of a recurring airway stricture or stenosis in an airway body lumen, the method comprising:

damaging, dilating, and/or removing the stricture or stenosis at a target site in the body lumen;

inserting a scope and a balloon catheter into the target site, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

hydrating and/or soaking the coating in the flushing composition at the target site;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated to activate the coating.

Embodiment 80 provides a method of treatment of chronic rhinosinusitis with nasal polyps (CRSwNP), the method comprising:

removing at least one of the nasal polyps at a target site in the body lumen;

inserting a scope and a balloon catheter into the target site in a body lumen, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated to activate the coating.

Embodiment 81 provides a method of treatment of laryngostenosis and/or subglottic stricture or stenosis, the method comprising:

damaging, dilating, and/or removing the laryngostenosis and/or subglottic stricture or stenosis at a target site in the body lumen;

inserting a scope and a balloon catheter into the target site in a body lumen, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated to activate the coating.

Embodiment 82 provides a method of treatment of severe asthma, the method comprising:

inserting a scope and a balloon catheter into a target site in a body lumen comprising a trachea, mainstem bronchus, *bronchus intermedius*, and/or a lobar bronchus, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated outside of the body to activate the coating.

Embodiment 83 provides a method of reduction of exacerbation of and/or hospitalization for severe asthma, the method comprising:

inserting a scope and a balloon catheter into a target site in a body lumen comprising a trachea, mainstem bronchus, *bronchus intermedius*, and/or a lobar bronchus, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated outside the body to activate the coating.

Embodiment 84 provides a method of reducing a concentration of bronchial smooth muscle cells of a severe asthma patient, the method comprising:

inserting a scope and a balloon catheter into a target site comprising bronchial smooth muscle cells in a body lumen, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated outside the body to activate the coating.

Embodiment 85 provides a method of reducing a concentration of eosinophils, IL-4, IL-5, IL-6, IL-13, IL-23, and/or ILC2 in an airway tract, the method comprising:

inserting a scope and a balloon catheter into a target site in a body lumen comprising a trachea, mainstem bronchus, *bronchus intermedius*, and/or a lobar bronchus, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated to activate the coating.

Embodiment 86 provides a method of treatment of a mucous plug in an airway, the method comprising:

removing mucous plug from a target site in a body lumen;

inserting a scope and a balloon catheter into the target site, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated to activate the coating.

Embodiment 87 provides a method of reduction of concentration of goblet cells in an airway tract, the method comprising:

inserting a scope and a balloon catheter into a target site comprising one or more goblet cells in a body lumen, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated to activate the coating.

Embodiment 88 provides a method reducing a concentration of one or more mucins in the airway tract, the method comprising:

inserting a scope and a balloon catheter into a target site in a body lumen comprising a trachea, mainstem bronchus, *bronchus intermedius*, and/or a lobar bronchus, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein prior to inflation the drug coated balloon is soaked and/or hydrated to activate the coating.

Embodiment 89 provides a method of treatment of chronic rhinosinusitis with nasal polyps (CRSwNP) and asthma, the method comprising:

removing at least one of the nasal polyps at a first target site in a first body lumen;

inserting a first scope and a first balloon catheter into the first target site in the first body lumen, wherein the first balloon catheter comprises a first elongated balloon, and a first coating layer overlying an exterior surface of the first balloon, wherein the first coating layer comprises one or more first additives and an initial drug load of a first therapeutic agent chosen from paclitaxel, docetaxel, taxol, rapamycin, sirolimus, zotarolimus, everolimus, tacrolimus, an analogue thereof, and a combination thereof;

inflating the first balloon to a first inflation diameter such that the first coating layer contacts an interior of the first body lumen at the first target site;

deflating the first balloon;

withdrawing the first scope and the first balloon catheter from the first target site;

inserting a second scope and a second balloon catheter into a second target site in a second body lumen comprising a trachea and/or a bronchus, wherein the second balloon catheter comprises a second elongated balloon, and a second coating layer overlying an exterior surface of the second balloon, wherein the second coating layer comprises one or more second additives and an initial drug load of a second therapeutic agent chosen from paclitaxel, docetaxel, taxol, rapamycin, sirolimus, zotarolimus, everolimus, tacrolimus, an analogue thereof, and a combination thereof;

inflating the second balloon to an inflation diameter such that the coating contacts an interior of the second body lumen at the second target site;

deflating the second balloon;

withdrawing the second scope and the second balloon catheter from the target site;

optionally performing the treatment again at a third target site in a trachea and/or bronchus that is different than the second target site;

wherein prior to inflation or the first and/or second drug coated balloon, the first and/or second drug coated balloon is soaked and/or hydrated to activate the coating.

Embodiment 90 provides the method of Embodiment 89, wherein a time between the treatment of the second target site and the treatment of the third target site is 1 to 6 weeks.

Embodiment 91 provides the method of Embodiment 89, wherein the second target site comprises a bronchus.

Embodiment 92 provides the method of Embodiment 91, wherein the bronchus comprises a mainstem bronchus, *bronchus intermedius*, and/or a lobar bronchus.

Embodiment 93 provides the method of any one of Embodiments 89-92, wherein the asthma is severe asthma.

Embodiment 94 provides the method of any one or any combination of Embodiments 1-93 optionally configured such that all elements or options recited are available to use or select from.

What is claimed is:

1. A method of treatment of a recurring airway stricture or stenosis in an airway body lumen, the method comprising:

inserting a scope and a balloon catheter into a target site at the recurring airway stricture or stenosis in the airway body lumen, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein the airway body lumen comprises supraglottis, glottis, subglottis, mainstem bronchus, bronchus intermedius, lobar bronchus, or a combination thereof.

2. The method of claim 1, wherein prior to inflation the coating on the drug coated balloon is hydrated and/or soaked to activate the coating.

3. The method of claim 2, further comprising flushing the target site with a flushing composition comprising water and/or saline, and performing the hydrating and/or soaking of the coating in the flushing composition at the target site.

4. The method of claim 2, further comprising performing the hydrating and/or soaking of the drug coating outside the body with a flushing composition comprising water and/or saline prior to inserting the drug coated balloon into the target site.

5. The method of claim 4, wherein the method is free of flushing at the target site.

6. The method of claim 2, wherein the hydrating and/or soaking is performed for 0.1 minutes to 5 minutes.

7. The method of claim 1, further comprising damaging, dilating, and/or removing the stricture or stenosis at the target site in the body lumen prior to the insertion of the scope and balloon catheter into the target site.

8. The method of claim 7, wherein the damaging, dilating, and/or removing comprises surgical removal, electrocautery, laser ablation, cryoablation, radiofrequency ablation, mechanical debulking, rigid bronchoscopy dilation, knife-cutting, direct vision internal stricturotomy, use of an uncoated balloon to dilate the stricture or stenosis, or a combination thereof.

9. The method of claim 1, wherein the one or more additives are chosen from pentaerythritol ethoxylate, pentaerythritol propoxylate, pentaerythritol propoxylate/ethoxylate, N-acetylglucosamine, N-octyl-D-gluconamide, N-nonanoyl-N-methylglycamine, N-octanoyl-N-methyl glutamine, C6-ceramide, dihydro-C6-ceramide, cerabroside, sphingomyelin, galaclocerebrosides, lactocerebrosides, N-acetyl-D-sphingosine, N-hexanoyl-D-sphingosine, N-octonoyl-D-sphingosine, N-lauroyl-D-sphingosine, N-palmitoyl-D-sphingosine, sphingosine, polyethylene glycol (PEG) caprylic/capric diglycerides, PEG-8 caprylic/capric glycerides, PEG caprylate, PEG-8 caprylate, PEG caprate, PEG caproate, glyceryl monocaprylate, glyceryl monocaprate, glyceryl monocaproate, monolaurin, monocaprin, monocaprylin, monomyristin, monopalmitolein, monoolein, creatine, creatinine, agmatine, citrulline, guanidine, sucralose, aspartame, hypoxanthine, theobromine, theophylline, adenine, uracil, uridine, guanine, thymine, thymidine, xanthine, xanthosine, xanthosine monophosphate, caffeine, allantoin, (2-hydroxyethyl)urea, N,N'-bis(hydroxymethyl) urea, glycerol ethoxylate, glycerol propoxylate, trimethylolpropane ethoxylate, pentaerythritol, dipentaerythritol, crown ether, 18-crown-6, 15-crown-5, 12-5 crown-4, butylated hydroxytoluene (BHT), butylated hydroxyanisole (BHA), a phospholipid, a derivative thereof, and combinations thereof.

10. The method of claim 1, wherein the one or more additives comprise pentaerythritol ethoxylate, pentaerythritol propoxylate, or a combination thereof.

11. The method of claim 1, wherein the elongated balloon has a length of about 20mm to about 300 mm, and wherein the balloon has a main diameter that is a nominal inflated diameter of 1 mm to 50 mm.

12. The method of claim 1, wherein the balloon comprises at least one neck section on the balloon comprising a smaller diameter than a main diameter of the balloon when the balloon is inflated, the at least one neck section dividing the balloon into at least two main sections each having a diameter.

13. The method of claim 1, wherein the initial drug load is from about 1 microgram to about 20 micrograms of the therapeutic agent per square millimeter of the balloon, measured when the balloon is at its nominal inflated diameter.

14. The method of claim 1, wherein inserting the scope and the balloon catheter comprises:

inserting the balloon catheter through a lumen of the scope, or inserting the balloon catheter and the scope side-by-side.

15. The method of claim 1, wherein the scope is an endoscope, rhinolaryngoscope, rhinoscope, bronchoscope, cystoscope, or a combination thereof.

16. The method of claim 1, wherein the inflating is performed such that:

the ratio of the inflation diameter to a normative body lumen diameter at the target site is about 1.0 to about 20, the ratio of the inflation diameter to a normative body lumen diameter at the target site is about 1.0, 1.1, 1.2, or 1.31 to 10, the balloon is inflated to a pressure that is equal to or greater than a nominal pressure of the balloon, a stretch ratio of the inflated diameter of the balloon to a normative body lumen diameter at the target site is about 1.0 to about 20, or a combination thereof.

17. The method of claim 1, wherein the airway stricture or stenosis is a stricture or stenosis induced by repeated medication treatments, intubation, tracheostomy, tuberculosis infection, surgical removal, electrocautery, laser ablation, cryoablation, mechanical debulking, rigid bronchoscopic dilation, stent placement, balloon dilation, bronchial smooth muscle cells, eosinophils, IL-4, IL-5, IL-6, IL-13, IL-23, ILC2, mucus plug, goblet cells, fibrosis, cystic fibrosis, and/or one or more mucins.

18. The method of claim 1, wherein the method is a method of treatment of laryngostenosis and/or subglottic stricture or stenosis, wherein the method further comprises damaging, dilating, and/or removing the laryngostenosis and/or subglottic stricture or stenosis at a target site in the body lumen; or the method is a method of treatment of severe asthma, wherein the target site comprises a mainstem bronchus, bronchus intermedius, and/or a lobar bronchus; or the method is a method of treatment of, and/or a method of reduction of exacerbation of and/or hospitalization for, severe asthma, wherein the target site comprises a trachea, mainstem bronchus, bronchus intermedius, and/or a lobar bronchus, wherein the method is free of flushing the target site, wherein the method comprises hydrating and/or soaking the coating outside the body to activate the coating; or the method is a method of reducing a concentration of bronchial smooth muscle cells of a severe asthma patient, wherein the target site comprises bronchial smooth muscle cells in a body lumen; or the method is a method of reducing a concentration of eosinophils, IL-4, IL-5, IL-6, IL-13,IL-23, and/or ILC2 in an airway tract, wherein the target site comprises a trachea, mainstem bronchus, bronchus intermedius, and/or a lobar bronchus; or the method is a method of treatment of a mucous plug in an airway, wherein the method further comprises removing mucous plug from a target site in a body lumen prior to inflation; or the method is a method of reduction of concentration of goblet cells in an airway tract, wherein the target site comprises one or more goblet cells in a body lumen; or the method is a method of reducing a concentration of one or more mucins in the airway tract, wherein the target site comprises a trachea, mainstem bronchus, bronchus intermedius, and/or a lobar bronchus.

19. A method of treatment of a recurring airway stricture or stenosis in an airway body lumen, the method comprising:

inserting a scope and a balloon catheter into a target site at the recurring airway stricture or stenosis in the airway body lumen, wherein the balloon catheter comprises an elongated balloon, and a coating layer overlying an exterior surface of the balloon, wherein the coating layer comprises one or more additives and an initial drug load of a therapeutic agent chosen from paclitaxel, docetaxel, taxol, rapamycin, sirolimus, zotarolimus, everolimus, tacrolimus, an analogue thereof, and a combination thereof;

inflating the balloon to an inflation diameter such that the coating contacts an interior of the body lumen at the target site;

deflating the balloon; and withdrawing the scope and the balloon catheter from the target site;

wherein the recurring airway stricture or stenosis is a stricture or stenosis induced by eosinophils, IL-4, IL-5, IL-6, IL-13, IL-23, ILC2, goblet cells, cystic fibrosis, or a combination thereof.

\* \* \* \* \*